Figure 1:
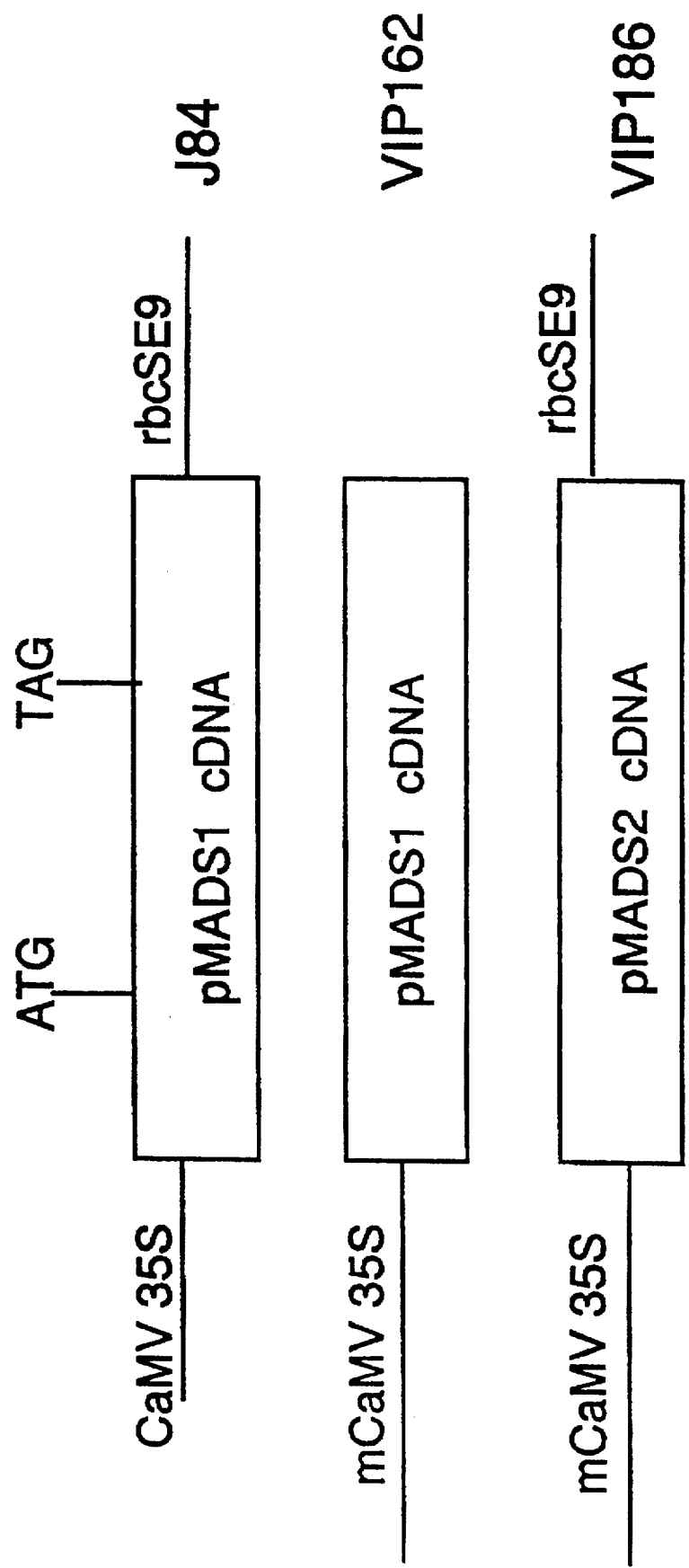

United States Patent [19]

Chua et al.

[11] Patent Number: 5,686,649
[45] Date of Patent: Nov. 11, 1997

[54] SUPPRESSION OF PLANT GENE EXPRESSION USING PROCESSING-DEFECTIVE RNA CONSTRUCTS

[75] Inventors: Nam-Hai Chua, Scarsdale, N.Y.; Alexander van der Krol, Utrecht, Netherlands

[73] Assignee: The Rockefeller University, New York, N.Y.

[21] Appl. No.: 375,222

[22] Filed: Jan. 19, 1995

Related U.S. Application Data

[63] Continuation of Ser. No. 216,229, Mar. 22, 1994, abandoned.

[51] Int. Cl.$^6$ .......................... A01H 4/00; C12N 15/82; C12N 5/14
[52] U.S. Cl. .................. 800/205; 435/172.3; 435/419; 800/250; 800/DIG. 67
[58] Field of Search .................. 435/172.1, 172.3, 435/320.1, 240.4; 800/205, 230, DIG. 67, 250

[56] References Cited

U.S. PATENT DOCUMENTS

| 5,034,323 | 7/1991 | Jorgensen et al. | 435/172.3 |
| 5,231,020 | 7/1993 | Jorgenson et al. | 435/172.3 |
| 5,283,184 | 2/1994 | Jorgensen et al. | 435/172.3 |

FOREIGN PATENT DOCUMENTS

WO 90/12084  3/1990  United Kingdom.
WO 92/06206  10/1991  United Kingdom.

OTHER PUBLICATIONS

Bird and Ray, "Manipulation of Plant Gene Expression by Antisense RNA," Biotechnology and Genetic Engineering Reviews, vol. 9, (Dec. 1991), pp. 207–227.
Jorgensen, "Altered Gene Expression in Plants due to Trans Interactions Between Homologous Genes," Trends Biotechnol., vol. 8, (Dec. 1990), pp. 340–344.
Hooper, "The Petunia Paradox: Added Copies of Genes Have Puzzling Effects in Plants," The Journal of NIH Research, vol. 3, (Dec. 1991), pp. 49–54.
Mattaj, "Splicing Stories and Poly(A) Tales: An Update on RNA Processing and Transport," Current Opinion in Cell Biology, vol. 2, (1990), pp. 528–538.
Izaurralde and Mattaj, "Transparent of RNA Between Nucleus and Cytoplasm," Seminars In Cell Biology, vol. 3, (1992), pp. 279–288.
de Carvalho et al., "Suppression of β–1,3–glucanase Transgene Expression in Homozygous Plants," EMBO J., pp. 2595–2602.
van der Krol et al., "Flavonoid Genes in Petunia: Addition of a Limited Number of Gene Copies May Lead to a Suppresion of Gene Expression," The Plant Cell, vol. 2, (Apr. 1990), pp. 291–299.
Napoli et al., "Introduction of a Chimeric Chalcone Synthase Gene into Petunia Results in reversible Co–Suppresion of Homologous Genes in Trans," The Plant Cell, vol. 2, (Apr. 1990), pp. 279–289.
van der Krol et al., "Functional Analysis of Petunia Floral Homeotic MADS Box Gene pMADS1," Genes & Development, vol. 7, (1993), pp. 1214–1228.
van der Krol et al., "Antisense Genes in Plants: An Overview," Gene, vol. 72, (1988), pp. 45–50.

Primary Examiner—Che S. Chereskin
Attorney, Agent, or Firm—Klauber & Jackson

[57] ABSTRACT

Disclosed is a novel method of suppressing plant gene expression. The suppression is achieved by transforming a plant with a DNA construct encoding a processing-defective RNA (pd-RNA constructs). A pd-RNA construct comprises a plant active promoter operably linked to a pd-RNA encoding segment (pd-RNA segment), wherein the pd-RNA segment comprises a sequence substantially homologous to the target gene and a defective intron and/or a defective 3' termination and processing sequence (hereinafter 3' processing sequence). The pd-RNA constructs of the present invention are designed to express target-gene-homologous RNA transcripts that are defective for messenger RNA processing. Various types of pd-RNA constructs are disclosed, including those defective for endonucleolytic cleavage or polyadenylation at the 3' end of the pd-RNA transcript and/or intron splicing. A pd-RNA construct of the invention may used to suppress a single, specific target gene or multiple target genes. Further, the suppression effect of a pd-RNA construct can be modulated and controlled through the use of an appropriate promoter.

8 Claims, 16 Drawing Sheets

SUPPRESSION OF PLANT GENE EXPRESSION USING PROCESSING-DEFECTIVE RNA CONSTRUCTS

This Application is a Continuation of application Ser. No. 08/216,229, filed Mar. 22, 1994, now abandoned.

1. INTRODUCTION

The present invention relates generally to the use of recombinant DNA methods for genetic engineering of plants. More particularly, this invention relates to a method of suppressing gene expression in plants by transforming plants with DNA constructs that encode processing-defective RNAs (pd-RNAs).

2. BACKGROUND OF THE INVENTION

The advent of recombinant DNA and gene transfer technologies have opened the way for plant scientists to genetically manipulate plant traits. Desirable manipulations include not only the introduction and expression of desirable novel genes but also the inhibition or suppression of undesirable resident genes, whether such genes are endogenous or exogenous in origin. To date, four methods exist for artificially suppressing or inhibiting gene expression: homologous recombination, ribozyme, antisense RNA, and cosuppression. Two of these, homologous recombination and ribozyme, remain problematic as artificial means of inhibiting gene activity in plants. Specifically, the utility of homologous recombination in modifying gene structure has been demonstrated in only a few specially constructed model systems (see Offringer et al. (EMBO J. 9:3077–84 (1990) and Kanevskii et al. (Dokl. Akad. Nauk. SSSR 312:1505–1507 (1990)). Consequently, homologous recombination remains unproven as a generally useful means of inhibiting or suppressing the activity of plant genes. The practical utility of ribozymes appears even more remote. Although engineered ribozymes have been used successfully to inactivate target RNAs in vitro, their ability to suppress gene expression in vivo has not been convincingly demonstrated. (See Castanotto, 1992, Crit. Rev. Eukaryot. Gen. Expr. 2:331–357 for a review of ribozyme research). In contrast, antisense RNA and cosuppression have been successfully used as means of suppressing plant gene activity. Both of these methods, however, remain relatively inefficient, as only a minority of the plants transformed with antisense RNA or cosuppression constructs express the desired level of target gene suppression or inhibition.

2.1 ANTISENSE RNA

Antisense RNA technology refers to the production and use of a RNA molecule that is complementary to the RNA transcript of the target gene. The ability of antisense RNA to inhibit gene activity was discovered in bacteria, where it is a natural mechanism of gene regulation. Antisense RNA appears to achieve its inhibitory effect by annealing with complementary RNA or DNA sequences and thereby interferes with several stages of gene expression, including DNA replication, RNA transcription, and RNA translation (See Simons, 1988, Gene 72:35–44 for a review of antisense RNA inhibition of bacterial gene expression).

In eukaryotes, antisense RNA appears not to be a natural mechanism of gene regulation. Nonetheless, antisense RNA has been adopted as a useful means of inhibiting gene expression in a wide variety of eukaryotic systems, including plants. See Bird and Ray, 1991, Biotechnol. Genet. Eng. Rev. 9:207–227 for a review of antisense RNA research and application in plants, which is incorporate herein by reference. Because eukaryotes differ from bacteria in gene structure and cellular organization, the mechanism of antisense RNA inhibition of eukaryotic gene expression remains unclear.

Antisense RNA is an imperfect means of inhibiting gene activity in plants. See id. In most instances, independent transformants containing the same antisense RNA construct vary widely in their suppression of target gene activity. Moreover, only a small minority of the transformants achieves strong suppression of the target gene expression. Thus, where the goal is a complete shut off of the target gene, the use of antisense RNA for such purposes is usually encumbered by the need to screen a large number of independent transformants for individuals with the desired level of inhibition.

2.2 COSUPPRESSION

Cosuppression is a recently discovered phenomenon of gene suppression in plants. See Jorgensen, 1990, Trend Biotechnol. 8:340–344, which is incorporated herein by reference. The phenomenon is often found in transgenic plants that have received one or more copies of a gene construct that are identical to or share nucleotide sequence homology with a resident gene. The term cosuppression derives from the observation that, in some of the transformants, suppression occurs for both the introduced gene as well as the resident homologue. The mechanism of cosuppression remains unclear. Proposed models range from fortuitous production of antisense RNA to anomalous chromosomal interactions between the introduced gene and the resident homologue. See Hooper, 1991, *The petunia paradox: added copies of genes have puzzling effects in plants*, J. NIH Res. 3:49–54, which is incorporated herein by reference.

As a means for inhibiting or suppressing gene expression in plants, cosuppression suffers the same deficiencies as antisense RNA. Like antisense RNA inhibition, cosuppression generally occurs in only a fraction of the independent transformants containing the cosuppression construct. Further, the extent of suppression usually varies among those exhibiting cosuppression. Thus, like antisense RNA, the use of cosuppression as a mechanism of gene inhibition also is usually encumbered by the need to screen a large number of independent transformants for individuals that express the desired level of inhibition or suppression.

2.3 ANTISENSE RNA AND COSUPPRESSION CONSTRUCTS

Antisense RNA and cosuppression constructs structurally resemble a messenger RNA encoding gene. Such constructs used in eukaryotes are typically composed of a "transcribed" RNA-encoding segment linked at its 5'-end to a type II RNA polymerase promoter and at its 3'-end to a transcription termination and 3' processing sequence. (The term "transcribed" segment is used herein to denote the sequence located between a promoter and a transcription and 3' processing signal.)

In cosuppression, the "transcribed" segment is either a part or the whole of a genomic or complementary DNA (cDNA) copy of the target gene. The "transcribed" segment is linked to the promoter in the sense orientation such that any RNA transcript produced from the segment is identical to a part or the whole of the mRNA of the target gene. In addition to being linked to a promoter and a 3' termination and processing sequence, the "transcribed" segment of cosuppression constructs may also contain one or more introns.

In antisense RNA constructs, the "transcribed" segment typically comprises a partial or complete cDNA copy of the target gene. The "transcribed" segment is linked to the promoter in the "inverted" orientation such that the transcripts produced are complementary to the messenger RNA of the target gene. Unlike cosuppression constructs, antisense RNA constructs seldom, if ever, include introns in the "transcribed" segment.

Because RNA polymerase II promoters are used to express antisense RNA and cosuppression constructs, RNA transcripts produced from such constructs can be expected to be processed like messenger RNA transcripts normally produced from such promoters.

2.4 POST-TRANSCRIPTIONAL PROCESSING OF MESSENGER RNA TRANSCRIPTS

Messenger RNA (mRNA) processing involves "capping" at the 5'-end and a coupled endonucleolytic cleavage and polyadenylation reaction at the 3'-end of the primary transcript. See Watson et al., *Molecular Biology of the Gene*, at 568–570 (4th ed. 1987). In addition, where the gene contains introns, the intervening sequences of the introns are spliced out from the transcript during the mRNA maturation process. See id. at 632–644. These processing steps, with the exception of the capping reaction, are regulated by specific signals on the primary RNA transcript.

Most eukaryotic messenger RNA, except histone mRNAs, are polyadenylated at their 3' ends. Generally, polyadenylation of mRNAs requires two regulatory sequences. See Mahle and Keller, 1992, Ann. Rev. Biochem. 61:419–440, for a review of 3' end processing of mRNA transcripts. One of the regulatory signals is a conserved AAUAAA hexanucleotide sequence, also known as the polyadenylation signal, located 15-30 nucleotides upstream of the 3' end of the mRNA. The other signal is a less conserved U- or GU-rich sequence located 3' downstream of the polyadenylation signal. In mRNA synthesis, transcription proceeds through both of these signals and terminates in a T-rich signal sequence further downstream (Kerppola and Kane, 1990, Biochemistry 29:269–278). See also Tantravahi et al., 1993, Molec. Cell. Biol. 13:578–587. Correct termination of transcription apparently requires all three signals. Deletion of any one signal results in the production of "run-on" transcripts. Spacing of these elements also appears to affect efficient termination (Tantravahi et al., ibid). Correct 3' processing, on the other hand, requires only the polyadenylation signal and the U-/GU-rich sequence. Removal of either signal results in aberrant 3' processing. The termination signal appears not to be required for normal 3' processing. The polyadenylation signal and the U-/GU-rich sequence operates normally even on "run-on" transcripts. See Chodchoy et al., Molec. Cell. Biol. 11:497–509 and reference cited therein. That is the primary transcript is cleaved somewhere between the two signals and the newly released 3' end polyadenylated.

Some yeast and plant genes that encode polyadenylated mRNAs do not contain the AAUAAA polyadenylation signal (Joshi, 1987, Nucleic Acids Res. 13:3791–9640). Studies have shown that in yeast some other as yet undefined signal at the 3' untranslated region of these messenger RNAs serves the same role as the AAUAAA sequence in controlling the endonucleolytic cleavage and polyadenylation reactions (Hyman et al., 1991, Molec. Cell. Biol. 11:2004–2012). Mutation or deletion of this alternate signal has the same consequence on mRNA processing as those affecting the AAUAAA polyadenylation signal: the abolishment of normal transcription termination and 3' end polyadenylation.

The 3' end of mature histone mRNA is produced by a specialized RNA processing event that does not involve polyadenylation. Unlike other types of mRNAs, a histone mRNA does not have a polyadenylation signal. Instead a highly conserved stem-loop structure at the 3' untranslated region of histone mRNA regulates 3' processing. This structure together with a purine-rich sequence located 3' downstream define the site of an endonucleolytic cleavage of the histone primary transcript to form the unmodified 3' end of mature histone mRNA.

The splicing of the intervening sequences of introns from messenger RNA transcripts is thought to precede or occur simultaneously with 3' processing. Although the exact mechanism of intron recognition and splicing remains to be elucidate, the structural elements of introns are well established. See Green, 1991, Ann. Rev. Cell Biol. 7:559–599. These elements include the conserved sequences at the 5' and 3' splice sites that demarcate the ends of an intron, and a branchpoint sequence TACTAAC located towards the 3' end of the intron. Animal and plant introns appear to have another important structure. In animals it is a polypyrimidine tract between branchpoint and the 3' splice site; whereas in some plants, a AU-rich tract serves the same role as the polypyrimidine tract in intron recognition and splicing. See Godall and Filipowicz, 1989, Cell 58:473–483.

Deletion of any of these elements from an intron abolishes the splicing out of the affected intron sequence or results in aberrant splicing of the entire RNA transcript. Mutations in the 5' and 3' splice site sequences can also result in defective splicing reactions (Chang and Sharp, 1989, Cell 59:789–795).

The correct splicing of introns and processing of 3' ends in messenger RNA transcripts seem to be required for export of mRNAs from the nucleus. See Izaurralde and Mattaj, 1992, Seminars in Cell Biol. 3:279–288; Zapp, 1992, Seminars in Cell Biol. 3:289–297. This requirement is deduced from evidence showing that defective splicing or 3' processing blocks the nuclear export of the affected messenger RNA transcripts. The exact basis of this processing dependent export remains unclear. Because mRNA export apparently involves transport mechanisms, one plausible explanation of the processing requirement is that the transport mechanism can some how recognize mature mRNA features. Alternatively, processing-defective RNA transcripts may be precluded from export by being locked up in dead-end processing complexes that block interactions between the RNA and the requisite transport mechanisms.

3. SUMMARY OF THE INVENTION

The present invention provides a method of producing plants exhibiting one or more desired phenotypic traits using processing-defective RNA constructs to suppress gene expression in the plant. The invention is based in part on the surprising finding that desired plants suppressed for specific trait(s) can be isolated from transgenic plants engineered with DNA constructs that encode processing-defective RNAs (hereinafter pd-RNA constructs).

The suppression of a target gene in transgenic plants is achieved by constructing and transforming with a pd-RNA construct comprising a pd-RNA encoding segment (hereinafter pd-RNA segment) operably linked to a type II RNA polymerase promoter, wherein the pd-RNA segment comprises a sequence substantially homologous to the target gene and a defective intron or a defective 3' termination and processing sequence (hereinafter 3' processing sequence). Unlike prior art antisense RNA and cosuppression constructs, pd-RNA constructs of the present invention are specifically designed to yield target-gene-homologous RNA transcripts that are defective for messenger RNA processing.

Accordingly, several types of pd-RNA constructs may be engineered. One type is prepared by omitting from the pd-RNA segment one or more of the signals required for endonucleolytic cleavage or polyadenylation at the 3' end of the pd-RNA transcript, such that the 3' end of the pd-RNA transcript will not be correctly processed. A second type is prepared by incorporating one or more defective introns into the pd-RNA segment, such that the intron's intervening sequence (IVS) will not be correctly spliced out of the pd-RNA transcript. A third type is prepared by incorporating a defective intron and a defective 3' processing sequence, such that the pd-RNA transcript will not correctly spliced or 3' processed.

A pd-RNA segment of the instant invention can comprise a sequence that is homologous to only one target gene. Such a pd-RNA construct would be useful for suppressing the expression of that specific target gene. Alternatively, a pd-RNA construct can have a pd-RNA segment that comprises several different segments, each homologous to a different target gene. Such a pd-RNA construct would be useful for the simultaneous suppression of multiple target genes. Further, the suppression effects of pd-RNA constructs can be modulated by the use of operably linked promoters that have different tissue- and developmental-specificities as well as expression strength.

The pd-RNA constructs of the present invention can be used to suppress the expression of any gene that is transcribed by a RNA polymerase II promoter. Such types of target genes include, but are not limited to mRNA, antisense RNA, and ribozyme encoding genes.

The instant invention have a variety of uses in regulating gene expression in plant cell cultures or in transformed plants. Plant cells can be transformed with pd-RNA constructs using a variety of methods including but not limited to Agrobacterium T-DNA, microprojectile bombardment, protoplast transformation, and electroporation. Plants containing pd-RNA constructs, in turn, can be regenerated from transformed cells.

The use of pd-RNA constructs in regulating gene expression may have particular value in engineering of agronomically important plants. These constructs would enable novel manipulation of phenotypic traits in engineered plants and may be beneficially used to produce transgenic plants that have enhanced nutritional value or processing properties; that have modified differentiation and development programs; or that have important novel commercial or industrial uses.

The invention is illustrated herein by way of two working examples. One involves the transformation of petunia with a pd-RNA construct encoding a floral homeotic gene, pMADS1. The other involves the transformation of petunia with a pd-RNA construct encoding a flower pigmentation gene, chalcone synthase (CHS). In both instances, the pd-RNA constructs used omitted 3' end processing signals downstream of the polyadenylation signal, e.g. the U-/GU-rich sequence and the T-rich termination sequence. Plants transformed with the pMADS1 pd-RNA construct show a high incidence of suppression of pMADS1 gene activity, as evidence by inhibition of petal differentiation in the second whorl of the flowers. Plants transformed with the CHS pd-RNA construct show a high incidence of suppression of CHS gene activity, as evidence by a loss of flower pigmentation.

3.1 DEFINITIONS

The terms listed below, as used herein, will have the meaning indicated.

CaMV=Cauliflower Mosaic Virus
cDNA=complementary DNA
CHS=chalcone synthase
DNA=deoxyribonucleic acid
PCR=polymerase chain reaction
poly (A)=polyadenylated
rbcS=ribulose biscarboxylase S
RNA=ribonucleic acid
transgenote=transformed plant or progeny of a transform plant

4. DESCRIPTION OF THE FIGURES

The file of this patent contains at least one drawing executed in color. Copies of this patent with color drawings will be provided by the Patent and Trademark Office upon request and payment of the necessary fee.

FIG. 1. pMADS1 expression and pd-RNA suppression constructs.

Figure 2:
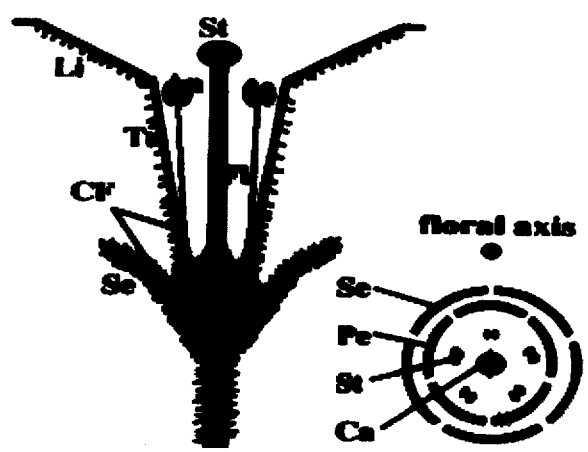
Figure 3A:
Figure 3B:
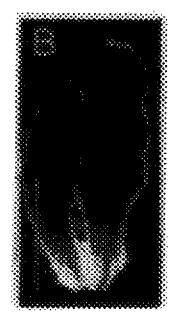
Figure 3C:
Figure 3D:
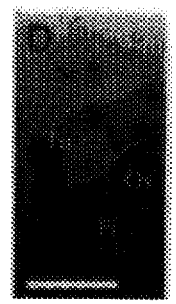
Figure 3E:
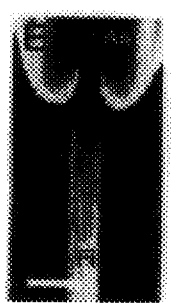
Figure 3F:
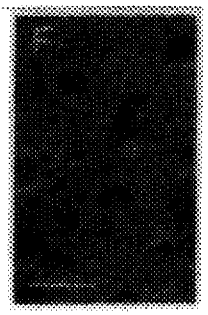
Figure 3G:
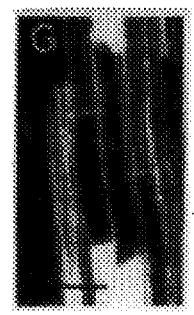
Figure 3H:
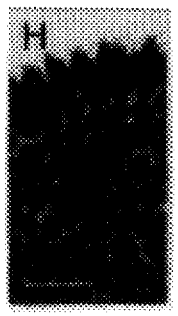
Figure 3I:
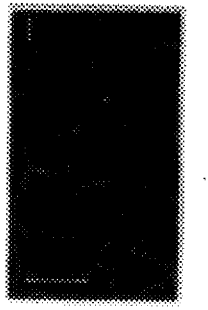
Figure 3J:
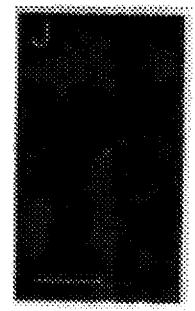
Figure 4A:
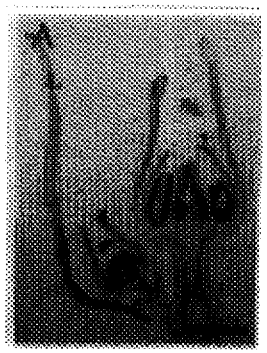
Figure 4B:
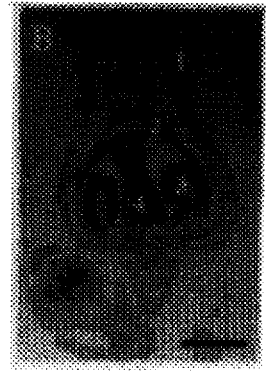
Figure 4C:
Figure 4D:
Figure 4E:
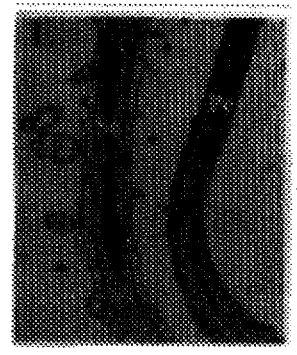
Figure 4F:
Figure 5A:
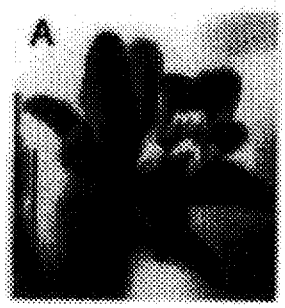
Figure 5B:
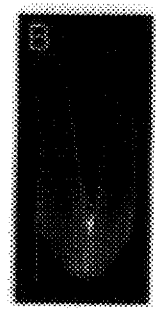
Figure 5C:
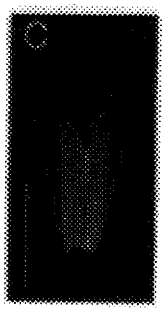
Figure 5D:
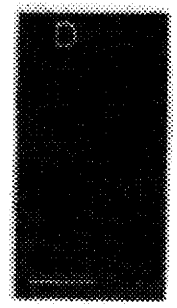
Figure 5E:
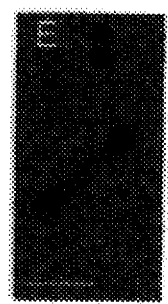
Figure 5F:
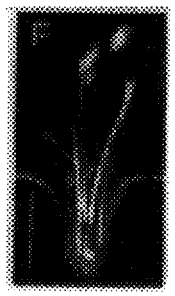
Figure 5G:
Figure 5H:
Figure 5I:
Figure 5J:
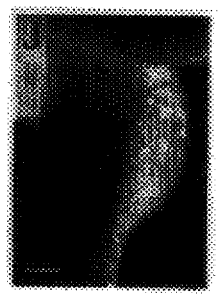
Figure 6A:
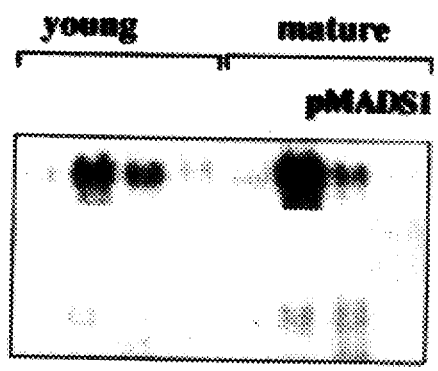
Figure 6B:
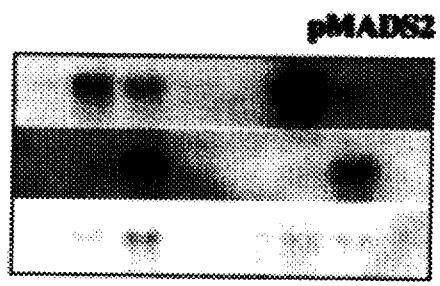
Figure 6C:
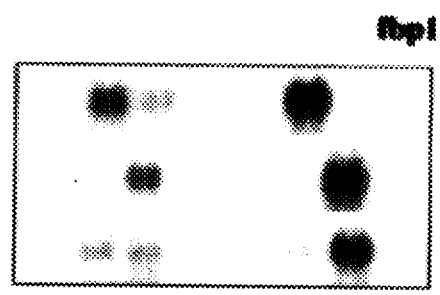
Figure 6D:
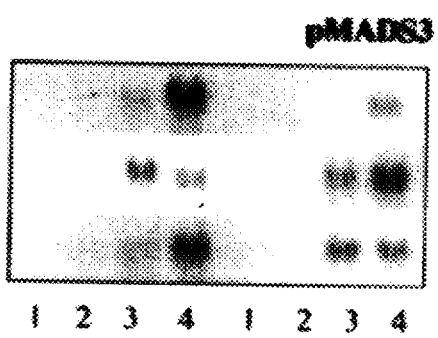
Figure 6E:
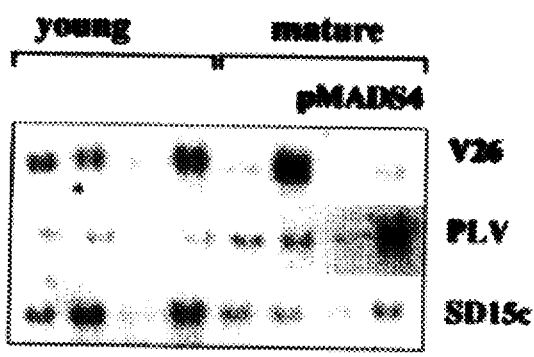
Figure 6F:
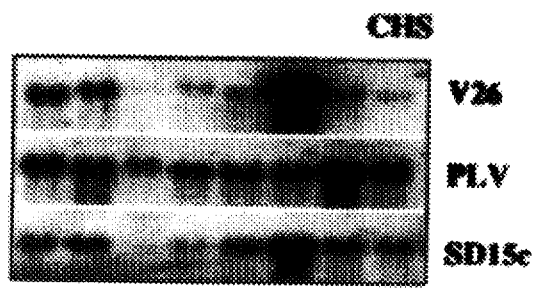
Figure 6G:
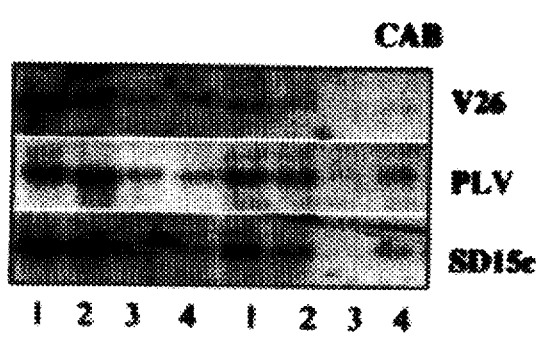
Figure 6H:
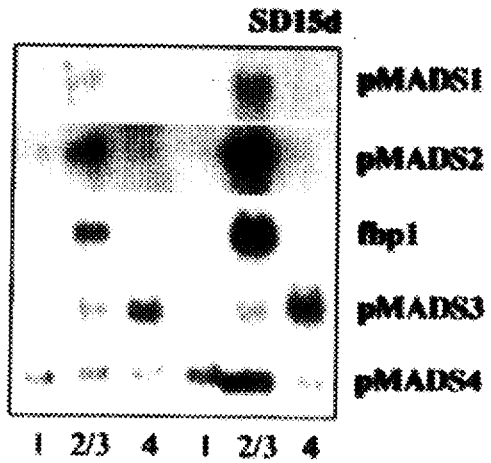

FIG. 2. Schematic diagrams of the *Petunia hybrida* wild type flower (V26).

Left Panel. A longitudinal section illustrating the fusion of the stamen filaments to the corolla tube and the faces on which trichomes can be detected. CF (congenital fusion) indicates the region where the stamen filament is fused to the corolla tube. (Se) Sepal; (Li) corolla Limb; (Tu) corolla Tube; (An) anther; (St) style and Stigma; (Ov) ovary.

Right Panel. Floral diagram. (Se) Sepal; (Pe) Petal; (St) stamen; (Ca) carpel.

FIG. 3. The petunia V26 flower.

Panel A. A V26 flower.

Panel B. Two sepals from the first whorl. (Note that the sepals are fused at the base, which contains less chlorophyll.)

Panel C. A longitudinal-cut flower bud with two sepals removed. (Note the stamen filaments (Fi) that are fused near the base to the corolla tube (Tu) and the trichomes at the outer face of the corolla tube.)

Panel D. A stained cross section of a V26 flower bud, near the base, showing the fusion of the filaments to the corolla tube.

Panel E. Close-up of a stamen filament near the anther.

Panel F. An upper epidermal peel from the first whorl sepal tissue.

Panel G. An epidermal peel from the adaxial face of the second whorl tube tissue.

Panel H. An upper epidermal peel from the second whorl petal limb.

Panel I. A lower epidermal peel from the second whorl petal limb, between the main veins.

Panel J. A lower epidermal peel from the second whorl petal limb, near the main vein.

(Tu) Tube; (Se) sepal; (An) anther; (Fi) filament; (St) style; (Ov) ovary. Vertical bar, 1 cm; thick horizontal bar, 1 mm; thin horizontal bar, 0.1 mm.

FIG. 4. Sections of V26 and gp (PLV) flowers.

Panel A. A longitudinal section of a V26 inflorescence. The numbers indicate the whorl. (L) Leaf.

Panel B. A longitudinal section of a gp (PLV) inflorescence. The numbers indicate the whorl.

Panel C. A transverse section of a V26 flower.

Panel D. A transverse section of a gp (PLV) flower. (Note that the stamen filaments are not fused to the second whorl sepal tube (cf. FIG. 3, Panel D).)

Panel E. Close-up of a transverse section of a V26 flower, showing sepal and petal tissue.

Panel F. Close-up of transverse section of a gp (PLV) flower, showing first and second whorl sepals.

Numbers refer to the floral whorl. (L) Leaf; (Se) sepal; (Pe) petal; (St) style; (Ov) ovary; (An) anther; (Fi) filament. Vertical bar, 1 cm; thick horizontal bar, 1 mm; thin horizontal bar, 0.1 mm.

FIG. 5. The flower of gp (PLV).

Panel A. A mature gp (PLV) flower.

Panel B. Two sepals from the first whorl. (Note that the sepals are fused near the base.)

Panel C. Two sepals from the second whorl. (Note that the sepals are fused for half of their length.)

Panel D. An upper epidermal peel from the second whorl sepal.

Panel E. A lower epidermal peel from the second whorl sepal.

Panel F. A longitudinal section of a mature gp (PLV) flower. (Note that the stamen filaments are not fused to the second whorl sepals.)

Panel G. A sepaloid stamen often found in gp (PLV) flowers.

Panel H. A gp (PLV) flower at a late stage of development. (Note that the extra third whorl sepaloid organs can develop regions with petaloid characteristics (arrow).)

Panel I. Close-up of gp (PLV) flower with the first and second whorl sepals removed. (Note the stamen filaments (not fused to the second whorl organs) and a sepaloid sixth organ, initiated between the stamen (arrow).)

Panel J. Close-up of a gp (PLV) stamen filament, showing petaloid cells and trichomes.

Vertical bar, 1 cm; thick horizontal bar, 1 mm; thin horizontal bar, 0. 1 mm. For abbreviations, see legend to FIG. 3.

FIG. 6. Expression of MADS box genes and CAB in floral organs of V26, gp (PLV), and pd-RNA construct suppressed plants. Total RNA was isolated from young and mature flower buds of V26 (top sections), PLV (middle sections), and SD15c (bottom sections). Filters containing 7 μg of RNA per lane were hybridized to specific probes derived from the genes indicated:

Panel A. pMADS1;

Panel B. pMADS2;

Panel C. fbp1;

Panel D. pMADS3;

Panel E. pMADS4;

Panel F. CHS;

Panel G. CAB.

For Panels A to G, the panels within one box were derived from one filter; therefore, the strength of the hybridization signal can be compared directly within a box. Lanes 1, 2, 3, and 4 represent RNA isolated from whorls 1, 2, 3, and 4, respectively.

Panel H. Total RNA was isolated from young and mature flowers of transgenic line SD15d. Lane 2/3 represents RNA isolated from the combined second and third whorl tissues. Lanes 1 and 4 represent RNAs isolated from whorls 1 and 4, respectively.

Figure 7:
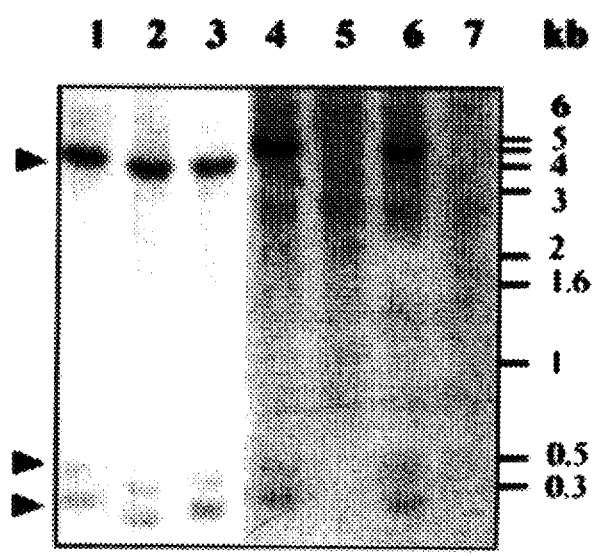
Figure 8A:
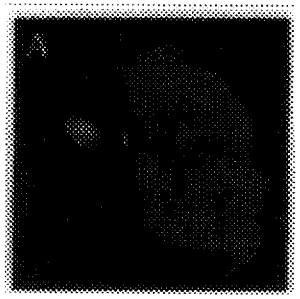
Figure 8B:
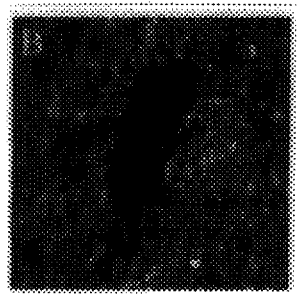
Figure 8C:
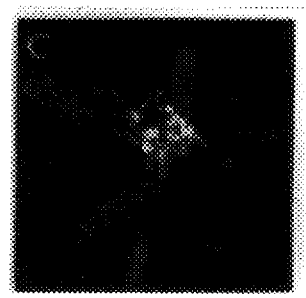
Figure 8D:
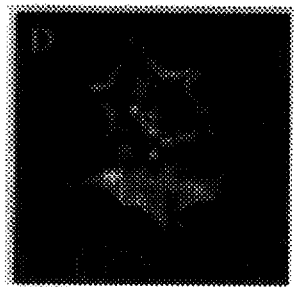
Figure 8E:
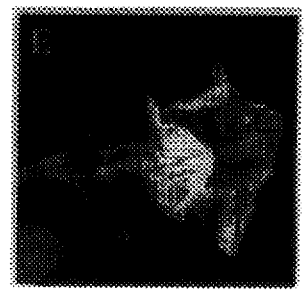
Figure 8F:
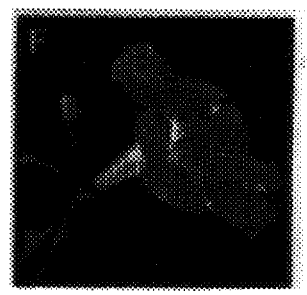
Figure 8G:
Figure 8H:
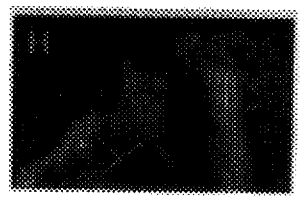
Figure 8I:
Figure 8J:
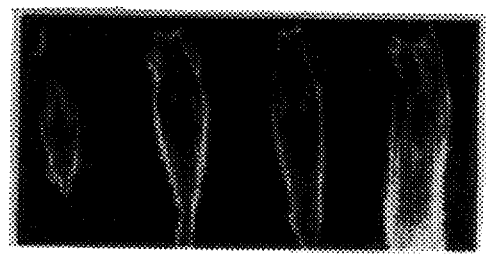
Figure 8K:
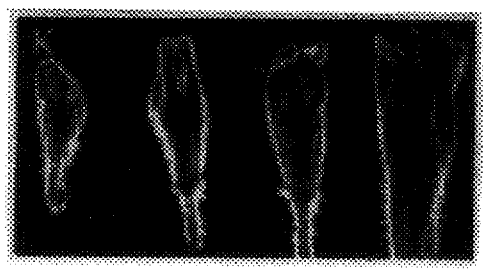
Figure 8L:
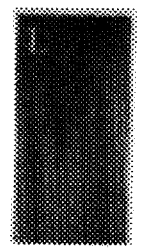
Figure 8M:
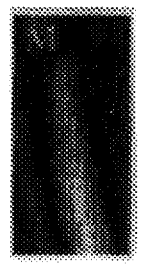
Figure 8N:
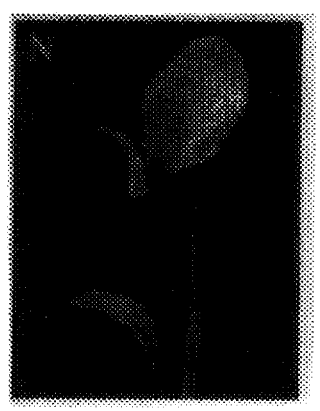

FIG. 7. Southern blot analysis of wild-type and gp (PLV) genomic DNA. Genomic DNAs were digested with HindIII, size fractionated on an agarose gel, and blotted onto a GeneScreen Plus filter. The blot was hybridized to a full-length pMADS1 cDNA (see Materials and Methods (Section 6.1)), and after hybridization it was washed under high-stringent conditions. The three pMADS1 gene fragments are indicated by arrows. (Lane 1) V26; (lane 2) V30; (lane 3) W115; (lanes 4-7) a segregating population of wild-type and gp (PLV) plants; (lanes 4, 6) wild-type plants; (lane 5, 7) gp (PLV) plants.

FIG. 8. Phenotypic analyses of flowers of pMADS1 restoration plants. Leaf tissue from hybrid GP/gp was used for transformation with the 35S-pMADS1 gene construct J84 (see Materials and Methods (Section 6.1)), and one transgenic line (M1) that showed an overexpression phenotype was back-crossed with gp (PLV). Genomic DNAs of progeny plants (M1a–z) were analyzed for the presence of wild-type pMADS1 and the 35S-pMADS1 transgene. Flowers of plants that did not carry the wild-type pMADS1 gene but contained one or more copies of the 35S-pMADS1 transgene (M1a–d) were analyzed (Panels B- to F).

Panel A. The transformed GP/gp plant that showed an overexpression phenotype (M1). This plant was crossed with gp (PLV), and M1 a–d are some of the progeny plants.

Panel B. Close-up of a M1b flower, showing a gp phenotype but with small sectors of petal tissue in the second whorl.

Panels C and D. A flower on M1b at a late stage of plant development, before and after anthesis. (Note the petal tissue that has developed after anthesis).

Panel E. M1c, heterozygous for the 35S-pMADS1 transgene.

Panel F. M1d, homozygous for the same 35S-pMADS1 transgene insert.

Panel G. Second whorl of M1b, showing the partial petal development.

Panel H. Close-up of second whorl of M1b. (Note the trichomes on the adaxial face of the petal).

Panel I. A corolla of M1c. (Note that the sepal structure can still be recognized through the corolla tissue, indicating that most of the corolla limb is derived from the second whorl (default) sepal).

Panel J. Flower buds of V25.

Panel K. Flower buds of M1 c.

Panel L. Inside of a V26 second whorl corolla tube. (Note the absence of trichomes on the adaxial face).

Panel M. Inside of a M1c second whorl corolla tube. (Note the presence of trichomes on the adaxial face).

Panel N. A petaloid stamen of M1c.

Vertical bar, 1 cm; thick horizontal bar, 1 mm; thin horizontal bar, 0.1 mm.

Figure 9A:
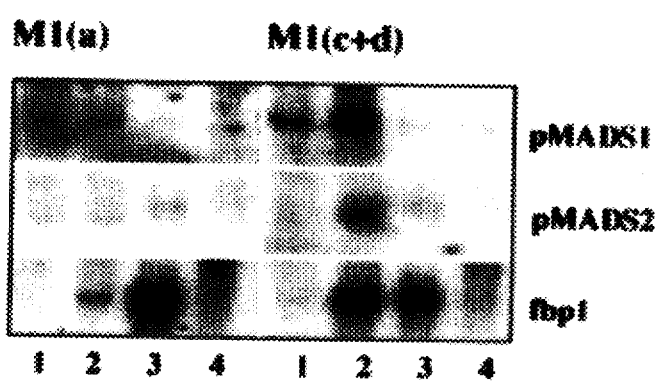
Figure 9B:
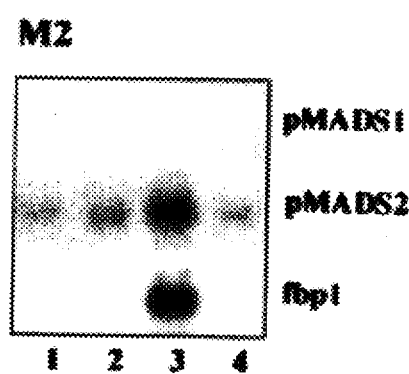
Figure 10A:
Figure 10B:
Figure 10C:
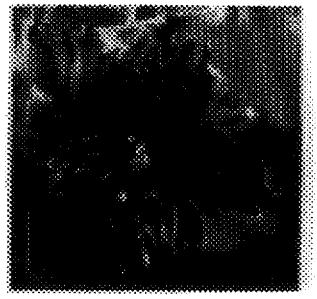
Figure 10D:
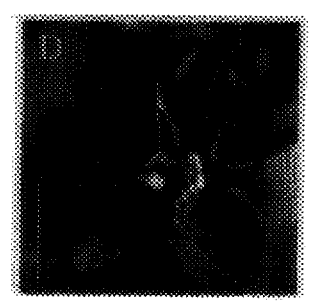
Figure 10E:
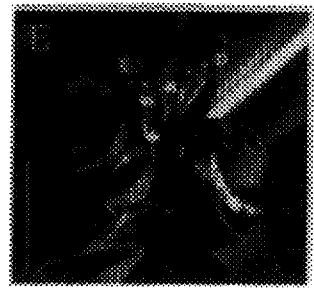
Figure 10F:
Figure 10G:
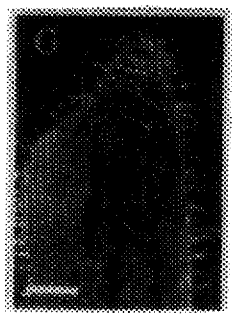
Figure 10H:
Figure 10I:
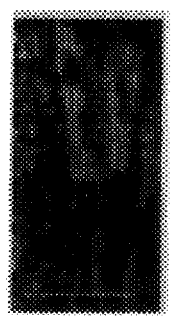
Figure 10J:
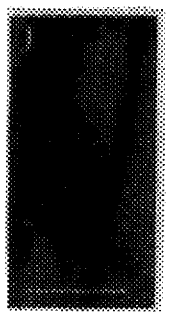
Figure 10K:
Figure 10L:
Figure 10M:
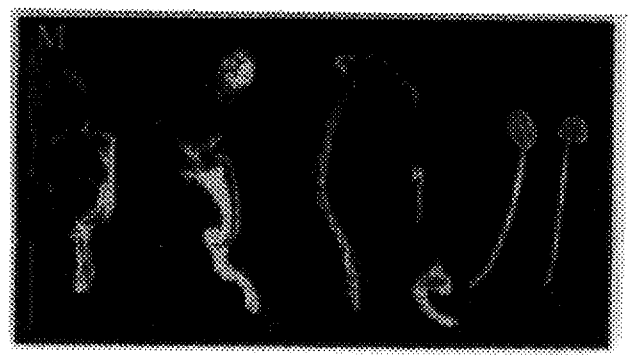

FIG. 9. Northern blot analysis of gp transgenic plants expressing pMADS1 or pMADS2. Total RNA was isolated from mature flower buds of gp (PLV) transgenic plants expressing the 35S-pMADS1 transgene J84 (Panel A) or the 35S-pMADS2 transgene VIP186 (Panel B). Equal amounts (7 μg) of RNA were analyzed on identical Northern blots using gene-specific probes. Lanes 1, 2, 3, and 4 represent RNA isolated from whorls 1, 2, 3, and 4, respectively. The signal for pMADS2 and fbp1 in B can be compared directly with the signal in FIG. 6, Panels B and C, respectively (same hybridization).

Panel A. In M1 (a) the expression of the 35S-pMADS1 transgene is very low and can only be detected in the third and fourth whorls upon prolonged exposure. In these transgenic plants the expression of pMADS2 and fbp1 is primarily in the mature third whorl. In M1(c+d) the average expression of the 35S-pMADS1 transgene is higher in all four whorls. In these plants the expression of pMADS2 and fbp1 is up-regulated in the second whorl, compared with nontransformed gp plants (cf. FIG. 6, Panels B and C).

Panel B. Transgenic gp plants that express the 35S-pMADS2 transgene (M2). Tissue from five independent transgenic flowers was combined for Northern analysis. The average expression of pMADS2 in the first, second, and fourth whorls is low (presumably from the transgene) and has no effect on the expression of fbp1 (cf. FIG. 6, Panel C).

FIG. 10. Phenotypic analysis of pMADS1 pd-RNA construct suppressed plants. Wild-type petunia plants (V26) were transformed with a 35S-pMADS1 pd-RNA construct (VIP162). Transgenic plant SD15 was selfed, and flowers of progeny plants (SD15a-d), showing different degrees of suppression, were analyzed.

Panel A. SD 15a. Although the effect on second whorl petal development is mild, the third whorl stamen filaments are not fused to the petal tube of this flower.

Panel B. SD12. The tube and petal tissue of this flower are not fully developed.

Panel C. SD15b. The second whorl tube is much reduced, and in the limb, sectors of petal or petaloid tissue have developed.

Panel D. SD15c. The flowers from his line are an almost complete phenocopy of gp (PLV) flowers.

Panel E. SD15c. Same flower as in Panel D, but 1 week later. After anthesis the second whorl can develop some petaloid characteristics.

Panel F. Inside of a SD15b flower. Part of the first and second whorl organs were removed to show that the stamen filaments are not fused to the second whorl organs and that extra, third whorl sepaloid organs develop in this flower (arrow).

Panel G. Second whorl sepaloid structure of SD3, showing sectors of petal tissue.

Panel H. Close-up of second whorl sepaloid structure of SD3, showing sectors of green cells, white cells, and cells pigmented with anthocyanin.

Panels I and J. An epidermal peel from SD3 second whorl tissue (see Panel H), showing small, fully pigmented petal cells next to nonpigmented and slightly pigmented jigsaw-shaped epidermal cells.

Panel K. Close-up of a stamen filament of a SD3 flower, showing petaloid cells and trichomes.

Panel L. SD15d. Most of the second whorl organs in these flowers do not develop or are fused to the stamens.

Panel M. SD15d. All of the organs of the second/third whorl that are produced in one flower.

Vertical bar, 1 cm; thick horizontal bar, 1 mm; thin horizontal bar, 0.1 mm.

Figure 11:
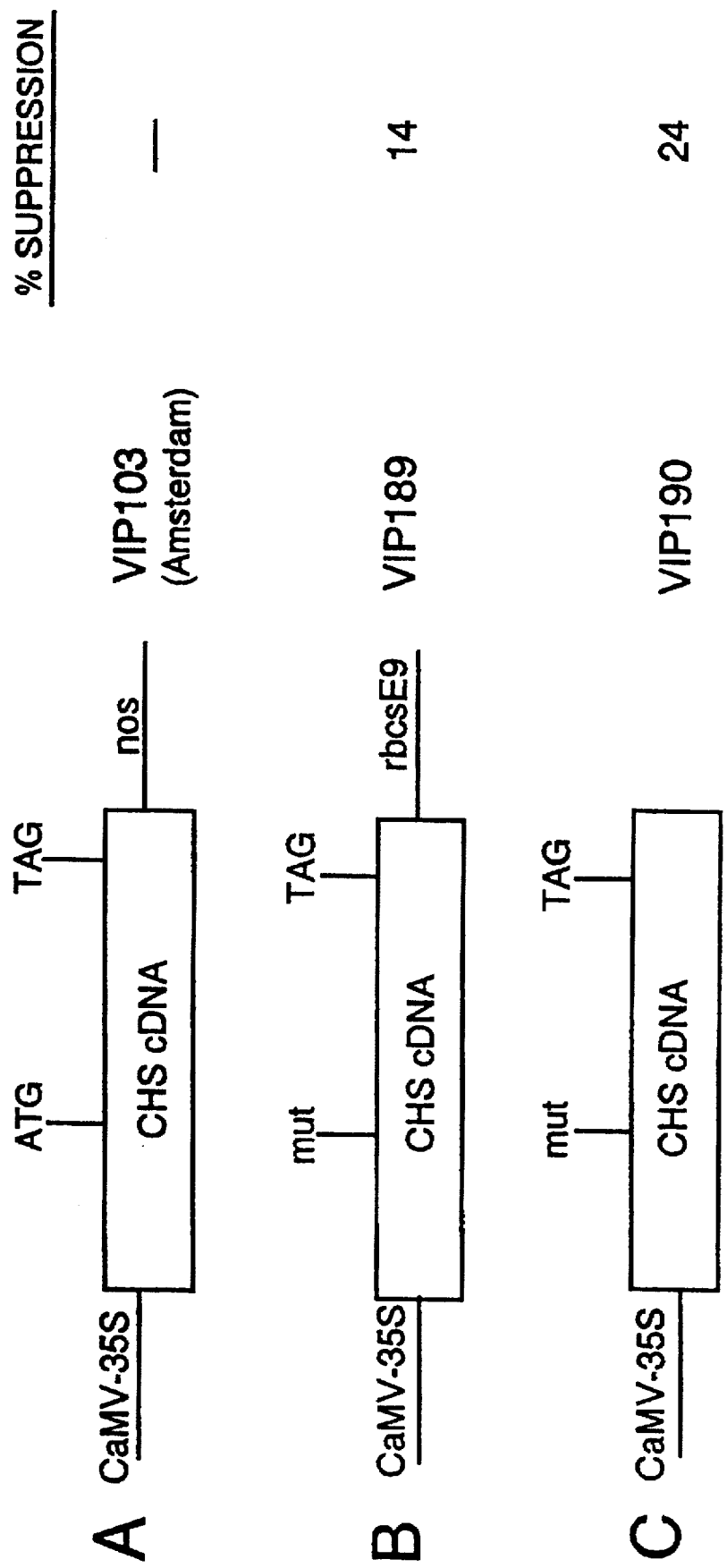

FIG. 11. The CHS pd-RNA constructs and their suppression activities. In VIP189 and VIP190, the initiation codon is mutated to a nonsense codon. "mut" indicates the location of this mutation.

Panel A. VIP103 construct.

Panel B. VIP189 construct.

Panel C. VIP190 construct.

5. DETAILED DESCRIPTION OF THE INVENTION

The present invention provides novel methods for producing novel plants, the plants so produced and the methods of their use. The invention is based in part on the surprising discovery that suppression of a target gene be achieved by transforming plant cell with a DNA construct that encodes a pd-RNA segment operably linked to a RNA polymerase II promoter, wherein the pd-RNA segment comprises sequences homologous to the target gene and signals for defective messenger RNA processing of pd-RNA transcripts.

Accordingly—without intending to be limited to a particular mechanism—some transcription of pd-RNA segment and defective processing of the resultant transcripts are likely important to effecting suppression of the target gene. Similarly, the severity of suppression is likely related to the strength of the promoter operably linked to the pd-RNA segment. Further, the degree of sequence homology between the pd-RNA segment and the target gene also likely affects the effectiveness of suppression of the target gene.

In accordance with the present invention, a pd-RNA construct comprises promoter operably linked to a pd-RNA segment containing sequences substantially homologous to the target gene. The pd-RNA segment further includes a defective intron and/or omits, at its distal 3' end, one or more of the signals required for transcription termination and 3' processing of any RNA transcribed from the linked promoter.

Depending on the pd-RNA segment and its operably linked promoter, plants transformed with a pd-RNA construct will exhibit a variety of different phenotypic traits. In particular, selecting plants with varying degree and kind of suppression of the target gene can be readily achieved in accordance with the present invention.

By the way of example, and not limitation, two embodiments of the present invention entail introducing pd-RNA constructs into petunia cells. The example pd-RNA constructs comprise a complementary DNA (cDNA) copy of a floral homeotic pMADS1 gene or a floral pigmentation CHS gene, each operably linked to a cauliflower mosaic virus 35S (CaMV 35S) promoter. Both pd-RNA constructs omitted, at the 3' end of the CaMV 35S-cDNA fusion, the U-/GU-rich and the T-rich sequences required for endonucleolytic cleavage and transcription termination, respectively, of primary messenger RNA transcripts.

The transformed cells are regenerated into petunia plants. Plants exhibiting altered flower development or pigmentation are selected from lines transformed with pMADS1 or CHS pd-RNA constructs, respectively. Except for the traits encoded by the target pMADS1 or CHS genes, the selected plants exhibit substantially all of the characteristics of untransformed petunia plants. Those skilled in the art will readily appreciate that other plants, other traits, other target gene sequences and the like may be substituted in accordance with the following guidelines.

5.1 TARGET GENES

The present invention can be used to suppress the expression of a wide range of target genes in plants. The present invention can be most advantageously used to suppress genes that alter selectable traits because such alterations often afford simple and direct means of identifying and isolating the affected plants. Categories of such selectable traits include, but are not limited to, visible traits, disease related traits, stress related traits, environmental traits, and processing traits.

The present invention can also be advantageously used to suppress target genes affecting screenable traits, which generally pertain to, but are not limited to, altered metabolic pathways. The identification and isolation of engineered plants with suppressions of such traits can be achieved through the use of appropriate biochemical and physical assay procedures. See Somerville and Brouse, 1991, Science 252:80–87 and Lemieux et al., 1990, Ther. Appl. Genet. 80:234–240, for examples of using massive, biochemical screening as a means of isolating plants with altered metabolism. Agronomically important metabolic processes and pathways that the present invention can be advantageously used to manipulate include, but are not limited to, photosynthesis, carbon fixation, sugar and carbohydrate metabolism, nitrogen assimilation and transport, amino acid biosynthesis, lipid biosynthesis, and secondary metabolite biosynthesis.

5.2 PROCESSING-DEFECTIVE RNA CONSTRUCTS

The properties of the nucleic acid sequences are varied as are the genetic structures of various potential host plant cells. The preferred embodiment of the present invention will describe a number of features which an artisan may recognize as not being absolutely essential, but clearly advantageous. These include methods of isolation or synthesis of pd-RNA construct components, the methods of constructing pd-RNA constructs, the manipulations of pd-RNA constructs to be introduced into plant cells, certain features of pd-RNA constructs, and certain features of vectors associated with pd-RNA constructs.

Plants are the preferred sources of several components of the pd-RNA constructs. These components include the parts of the pd-RNA segment (e.g. the sequence that is homologous to the target gene, the introns, and the 3' termination and processing sequence) and its operably linked promoter. The intended host plant for the pd-RNA construct is the most preferred source of these components. However, other organisms may also serve as sources. In such instances, the sequence to serve as the pd-RNA encoding segment should share substantial nucleotide sequence homology with the target gene, and the other components, excepting for any intended defects, must be capable of proper functioning in the host plant.

The approaches and methods that can be used to build pd-RNA constructs are well known in the art. E.g., see Sambrook et al., 1989, *Molecular Cloning, a laboratory manual*, Cold Spring Harbor Laboratory Press, Plainview, N.Y. for detailed teachings of recombinant DNA methods that can be used to isolate, characterize, and manipulate the various components of pd-RNA constructs, as well as to built the constructs themselves. In some instances, where the sequence of the desired components or structures is known, it may be advantageous to synthesize such components and structures rather than isolating them from organisms. In those instances, an artisan can refer to teachings of the likes of Caruthers et al., 1980, Nuc. Acids Res. Symp. Ser. 7:215–233, and of Chow and Kempe, 1981, Nuc. Acids Res. 9:2807–2817. In other instances, the desired structures and components may be advantageously produced by polymerase chain reaction (PCR) amplification. For such teachings, an artisan can look to the like of Gelfand, 1989, PCR Technology, Principles and Applications for DNA Amplification, (Ed.), H. A. Erlich, Stockton Press, N.Y.; Current Protocols In Molecular Biology, Vol. 2, Ch. 15, Eds., Ausubel et al., John Wiley & Sones, 1988.

5.2.1 OPERABLY LINKED PROMOTERS

A number of promoters may be operably linked to the pd-RNA segment in accordance with the invention. Operably linked refers to a functional linkage between the promoter and the pd-RNA segment such that said promoter controls transcription of the pd-RNA segment in transformed plant cells.

RNA polymerase II promoters are the preferred promoters for the pd-RNA constructs. The RNA polymerase II promoter should be linked at a distance that is most efficient for transcription of the pd-RNA segment. This distance should be within about 500 nucleotides, preferably within 200 nucleotides and optimally within 50 nucleotides of the pd-RNA segment.

In effecting a total suppression of the target gene, the use of a strong and constitutive promoter would be advantageous. Examples of such strong constitutive promoters include, but are not limited to, the cauliflower mosaic virus 35S (CaMV 35S) promoter, the Ti plasmid mannopine synthase (MAS) promoter, and their derivatives. See Benfey et al., 1990, EMBO J 9:1677–1684, and references cited therein for descriptions of CaMV 35S and derivative promoters; Comai et al., 1990, Plant Molec. Biol. 15:373–381, and references cited therein for descriptions of MAS and derivative promoters.

In effecting suppression that is limited in pattern, it may be preferable to use promoters whose spatial and temporal expression patterns closely match that of the desired suppression pattern. Various regulated promoters may be advantageously used for achieving this type of suppression. For example, were the desired suppression pattern to be limited to leaves, preferred promoters may be leaf-specific promoters such as those of the ribulose-1,5-bisphosphate carboxylase and the chlorophyll a/b protein genes. Similarly, were the desired suppression pattern to be limited to seeds, the preferred promoters may be seed-specific promoters such as those of the various seed storage protein genes. It may also be advantageous to use artificially or modified promoters in order to achieve suppression levels and/or patterns that are not readily attainable with naturally occurring plant promoters. See Salina et al., 1992, Plant Cell 4:1485–1493, for examples of enhancer modified promoters that have novel expression patterns.

In selecting promoters for use in the present invention, the following considerations should be matched: (1) the promoter's expression pattern in the host cell to that of the desired suppression pattern, and (2) the promoter's strength to the desired degree of suppression, e.g. strong promoters for strong suppressions and weak promoters for weak suppressions.

Nonetheless, it is well known that the activity and expression pattern of a promoter may vary depending on its location in the plant genome. Thus, not all plant transformants of a given pd-RNA construct can be expected to yield identical pattern of suppression. Consequently, some screening of the transformants may be required to isolate those plants exhibiting the desired pattern of target gene suppression.

In accordance with the instant invention, it is only advantageous but not essential that a pd-RNA construct has the pd-RNA segment operably linked to a promoter. Because some transforming DNA typically fractures during transformation and the resulting fragments insert at random sites throughout the host genome, it is expected that some pd-RNA segments would be fortuitously inserted operably linked to endogenous promoters. And it is further expected that some such resident promoters would have the desired expression properties. Thus, it is possible to achieve the desired pattern of target gene suppression by transforming plants with a pd-RNA construct containing the pd-RNA segment without an operably linked promoter, albeit at a lower success rate than if a promoter-containing pd-RNA construct is used.

5.2.2 TARGET GENE HOMOLOGOUS SEQUENCES

The pd-RNA segment comprises in part sequences that are substantially homologous to the target gene to be suppressed (such sequences are referred to hereinafter as homologous sequences). It is desirable that the homologous sequence has at least 65% homology with the target gene nucleotide sequence. Higher homologies are likely to exert greater suppressive effects. Thus, where strong suppression is desired, homologous sequence with homologies of greater than about 80% is preferred and homologies of greater than about 95% to complete identity would be most preferred. The desired homologies may also be determined by the ability of the pd-RNA sequence to selectively hybridize with that of the target gene. In this respect, it is preferred that the pd-RNA sequence be capable of hybridizing with the target gene sequence under low stringency conditions. More preferred would be a pd-RNA sequence capable of hybridizing with the target gene sequence under moderate stringency conditions. And most preferred would be a pd-RNA sequence capable of hybridizing with the target gene sequence under high stringency conditions.

The homologous sequence within the pd-RNA segment need not be the full length of the target gene. A homologous sequence with greater than about 50–100 basepairs (bp) would be desirable. Longer homologous sequences are likely to exert greater suppressive effects. Thus, where strong suppression is desired, a homologous sequence of greater than about 200–300 bp is preferred, and a homologous sequence of greater than about 500 bp is especially preferred. However, a homologous sequence for the entire length of the target gene would be most preferred.

Since the pd-RNA segment need only be homologous to a portion of a target gene and still enable suppression, it is possible and practical to suppress multiple target genes with a single pd-RNA construct by using a pd-RNA segment comprising multiple homologous sequences fused together, with each sequence having homology to a different target gene.

In accordance with the present invention, the homologous sequence can corresponds to any transcribed region of the target gene, e.g. intron, exon or untranslated sequences. However, a sequence homologous to exons is preferred, and a sequence homologous to a full-length complementary DNA (cDNA) copy of the target gene is most preferred. Thus, the homologous sequence may be a piece of the genomic or cDNA copy of the target gene or a sequence substantially homologous to the target gene.

The orientation of the homologous sequence with respect to the operably linked promoter is not critical. Accordingly, in one embodiment of the invention, the homologous sequence is linked in the antisense orientation to the promoter. In this orientation, transcription from the promoter produces pd-RNA transcripts that are complementary to the RNA transcripts of the target gene. Nonetheless, the preferred linkage is in the sense orientation. In this orientation, transcription from the promoter produces pd-RNA transcripts that are complementary to the coding strand of the target gene. In both embodiments, there would be pd-RNA transcripts which are substantially homologous to the target gene. The two embodiments differ in that their would be pd-RNA transcripts are homologous to opposite strands of the target gene.

5.2.3 pd-RNA SEGMENTS CONTAINING DEFECTIVE 3' PROCESSING SEQUENCES

In accordance with the present invention, the pd-RNA segment includes one or more features that would cause improper processing of pd-RNA transcripts. The preferred features are those that would cause defective processing of RNA transcribed from RNA polymerase II promoters. Most preferably, the features are those that would cause defective processing of pre-messenger RNA (pre-mRNK) transcripts.

Accordingly, an embodiment of the present invention is a pd-RNA segment whose target gene homologous sequence is operably linked to a defective transcription termination and 3' processing sequence (3' processing sequence). Specifically, the defective 3' processing sequence is placed at the 3' end of the homologous sequence (where the operably linked promoter is at the opposite, 5' end), and in the correct orientation such that, were defects not present in the 3' processing sequence, it would effect correct transcription termination and 3' processing of pd-RNA transcripts. The placement of the defective 3' processing sequence is preferably no further than about 200–300 bp from the 3' end of the homologous sequence. It is highly preferable that the distance be less than 50–100 bp and most preferable that the 3' processing sequence be immediately contiguous to the homologous sequence.

The defective 3' processing sequence can be a naturally occurring one isolated from an eukaryotic organism. Alternatively, the defective 3' processing sequence can be created from a functional one isolated from the 3' end of an eukaryotic gene, most preferably from the 3' end of a plant gene. Since 3' processing sequences of mRNA encoding genes vary in length, a 3' processing sequence here refers to the genomic sequence that encodes the 3' untranslated region of the mature mRNA and sequences extending at least about 500–1,000 bp immediately 3' downstream of the 3' untranslated region.

A defective 3' processing sequence can be created from a functional 3' processing sequence by deleting or mutating one or more of the key structures required for transcription termination and/or 3' processing. Where the 3' processing sequence is from a non-histone gene, one useful type of defect is the deletion or mutation of the polyadenylation signal sequence, e.g. (AAUAAA or its equivalent sequence). Another type is the deletion or mutation of the U- or GU-rich sequence located downstream of the polyadenylation signal. A third type may be the deletion or mutation of the T-rich sequence located yet further downstream of the polyadenylation signal. Where the 3' processing sequence is originally from a histone gene, defective versions of the 3' processing sequence can be created by deleting or mutating the stem and loop structure and/or the downstream purine-rich sequence.

In creating defective 3' processing sequences, the complete and total mutation or deletion of the key structures is preferred over partial mutations or deletions. Further, additional useful defective 3' processing sequences can be created by combining two or more of the above described types of defects.

Where the pd-RNA segment consists of a cDNA that contains a polyadenylation signal sequence and the segment is placed in the "sense" orientation with respect to the linked promoter, a preferred embodiment of the pd-RNA construct is to omit attaching to the pd-RNA segment sequences containing the other 3' processing signals, e.g. the U-, or GU-rich sequence, or the T-rich sequence. Alternatively, sequences containing these other signals may be linked to the cDNA, provided the polyadenylation signal in the cDNA is mutated or deleted.

5.2.4 pd-RNA SEGMENTS CONTAINING DEFECTIVE INTRONS

Another embodiment of the present invention is a pd-RNA construct whose pd-RNA segment contains one or more defective introns. In these constructs, a defective intron can be placed 3' downstream of the operably linked promoter and 5' upstream of the 3' processing sequence, where a 3' processing sequence is present in the construct. Where the 3' process sequence is absent, a defective intron is placed no further 3' downstream of the promoter than the 3' end of the target gene homologous sequence. In all instances, the defective intron is placed in the sense orientation with respect to the promoter. That is the orientation which, were the intron not defective, would allow for the correct splicing out of the intron's intervening sequence (IVS) from the pd-RNA transcript.

The defective intron can be a naturally occurring one isolated from an eukaryotic organism, preferably a plant. Alternatively, a defective intron can be created from a normal intron, preferably a normal plant intron. Most preferably, a defective intron is created from an intron of the intended host plant.

A defective intron can be derived from a functional intron by deleting or mutating one or more of the intron's splicing signals. One useful type of defective intron contains deletion or mutation of the 5' splice site. Another type contains deletion or mutation of the 3' splice site. A further type contains deletion or mutation of the branchpoint sequence. A yet further type contains deletion or mutation of the AU-rich tract or its equivalent. In all instances, the complete deletion or mutation of each of the splice signals is preferred over any partial deletion or mutation.

In various embodiments of the invention, it may be desirable to incorporate both a defective 3' processing signal and defective intron into the pd-RNA segment.

5.3 RECOMBINANT CONSTRUCTS

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding β-glucuronidase (Jefferson, 1987, Plant Molec Biol. Rep 5:387–405), luciferase (Ow et al., 1986, Science 234:856–859), B protein that regulate anthocyanin pigment production (Goff et al., 1990, EMBO J 9:2517–2522).

In embodiments of the present invention which utilize the Agrobacterium tumefaciens system for transforming plants (see below), the recombinant constructs additionally comprise the left and right T-DNA border sequences flanking the DNA sequences to be transformed into plant cell. The proper design and construction of such T-DNA based transformation vectors are well known to those skilled in the art.

5.4 PRODUCTION OF TRANSGENIC PLANTS AND PLANT CELLS

A recombinant construct containing a pd-RNA construct, as described herein, is used to transform a plant cell or to genetic engineer plants. In a preferred embodiment, Agrobacterium tumefaciens is employed to introduce a pd-RNA-containing recombinant construct into plants. Such transformation preferably uses a binary Agrobacterium T-DNA vector (Bevan, 1984, Nuc. Acid Res. 12:8711–8721), and the co-cultivation procedure (Horsch et al., 1985, Science 227:1229–1231). Generally, Agrobacterium is used to transform dicotyledonous plants (Bevan et al., 1982, Ann. Rev. Genet 16:357–384; Rogers et al., 1986, Methods Enzymol. 118:627–641). Agrobacterium also may be used to transfer DNA to a wide range of monocotyledonous plants as well. (Hernalsteen et al., 1984, EMBO J 3:3039–3041; Hooykass-Van Slogteren et al., 1984, Nature 311:763–764; Grimsley et al., 1987, Nature 325:1677–179; Boulton et al., 1989, Plant Mol. Biol. 12:31–40.; Gould et al., 1991, Plant Physiol. 95:426–434).

Alternative methods for introducing pd-RNA recombinant constructs into plants and plant cells may also be utilized, particularly if the desired target is a monocotyledonous plant or plant cells. These methods include, but are not limited to, protoplast transformation through calcium-, PEG- or electroporation-mediated uptake of naked DNA (Paszkowski et al., 1984, EMBO J 3:2717–2722, Potrykus et al. 1985, Molec.. Gen. Genet. 199:169–177; Fromm et al., 1985, Proc. Natl. Acad. Sci. USA 82:5824–5828; Shimamoto, 1989, Nature 338:274–276) and electroporation of plant tissues (D'Halluin et al., 1992, Plant Cell 4:1495–1505). Other methods for transforming monocotyledonous plants include microinjection, silicon carbide mediated DNA uptake (Kaeppler et al., 1990, Plant Cell Reporter 9:415–418), and microprojectile bombardment (Klein et al., 1988, Proc. Natl. Acad. Sci. USA 85:4305–4309; Gordon-Kamm et al., 1990, Plant Cell 2:603–618).

The pd-RNA constructs may be introduced into a wide variety of plants and plant cell systems using the transformation methods mentioned above. In preferred embodiments of the invention, such transformed plants and plant cells include, but are not limited to, those of maize, wheat, rice, soybean, tomato, tobacco, carrots, potato, sugar beets, sunflower, yam, Arabidopsis, rape seed, and petunia.

Transformed cells and plants may be identified and isolated by selecting or screening for the marker genes present on the transforming DNA. Selections and screening methods in the various plant systems are well known to those skilled in the art. A number of physical and biochemical methods may be used, either independently or together with phenotypic selection or screening, to identify transformants containing the pd-RNA constructs. These methods include but are not limited to: 1) Southern analysis or PCR amplification for detecting and determining the structure of the recombinant DNA insert; 2) northern blot, S-1 RNase protection, primer-extension or reverse transcriptase-PCR amplification for detecting and examining the pd-RNA transcript; 3) enzymatic assays for detecting the protein products of the pd-RNA encoding segment, where the segment potentially encodes a functional enzyme or ribozyme; 4) protein gel electrophoresis, western blot techniques, immunoprecipitation, or enzyme-linked immunoassays, where such potential products are proteins. Additional techniques such as in situ hybridization, enzyme staining, and immunostaining, may be used to detect the presence or expression of the recombinant construct in specific plant organs and tissues. The methods for doing all of these assays are well known to those skilled in the art.

5.5. UTILITY OF THE INVENTION

The present invention may be advantageously used to regulate a variety of important plant traits. In particular embodiments of the invention, by way of illustration, and not by limitation, pd-RNA constructs encoding homologous sequences to flower-specific genes, such as a CHS pigmentation gene, a MADS-1 homeotic gene, etc., may be used to alter flower structure and development. See Mol et al., 1988, Plant Mol. Biol. Reporter 6:274–279 for a listing of cloned flower pigmentation genes. These alterations may allow for production of novel flowers of commercial interests or for artificial control of plant fertility, useful in plant breeding and hybrid seed production.

In other embodiments, pd-RNA constructs encoding homologous sequences to a fruit-ripening gene, such as a polygalacturonase gene, a ethylene biosynthetic gene, etc., may be used to alter fruit-ripening processes. See Bird and Ray, 1991, Biotechnol. Genet. Eng. Rev. 9: 207–27. These alterations may allow for production of fruits with longer shelf-lives, enhanced flavor or other commercially important traits.

In further embodiments, pd-RNA constructs encoding homologous sequences to lipid metabolism genes, such as stearyl desaturase, acetyl transacylase, etc. may be used to alter fatty acid and lipid compositions of plants. See Somerville et al., 1988, Recent Advances in Phytochemistry (Conn ed.), Plenum Press, pg. 19–44; Browse et al., 1989, "Strategies for Modifying Plant Lipid Composition", *Plant Gene Transfer* (Lamb et al. eds.) Alan Liss. These alterations may allow for the production of plant oils with enhanced nutritional qualities, processing properties or important industrial applications.

The present invention may also be advantageously used to alter sugar and carbohydrate metabolism of plants. The desired plants may be obtained by transformations with pd-RNA segments containing homologous sequences to genes such as starch synthetase, ADP-glucose pyrophosphorylase, amylase, etc. See generally, Bonner and Varner, 1976, *Plant Biochemistry* (3rd Ed) Academic Press, New York. These alterations may allow for the production of plants with enhanced processing or nutritional qualities as well as important commercial uses.

To the best of applicants' knowledge, this is the first report of gene suppression by transforming host cells with recombinant constructs that encode processing-defective RNA transcripts containing homologies to target genes. Clearly, such constructs can be used to modify gene expression for basic research as well as biotechnological applications.

6. EXAMPLE 1 pd-RNA CONSTRUCT ENCODING A pMADS1 cDNA SEQUENCE SUPPRESSES pMADS1 EXPRESSION IN PETUNIA

The suppression pattern conferred by a pd-RNA construct encoding sequences homologous to the pMADS1 gene was analyzed in petunia plants. The petunia MADS-box gene pMADS1 is a flower homeotic gene. Its role in regulating flower development is established by the observations that a petunia pMADS1 deletion mutant gp (PLV) displays anomalous flower development and that transformation of gp (PLV) with a functional pMADS1 gene restores normal flower development.

Transformation of wild-type petunia with a pd-RNA construct encoding pMADS1 produces transgenotes exhibiting the gp (PLV) phenotype. Namely, the flowers of the transformed plants show a homeotic conversion of the second whorl petal into sepal and anomalous stamen development. Analysis of the affected transgenotes show a reduction in the steady state mRNA levels of the pMADS1 gene and of the related pMADS2 gene.

6.1 MATERIALS AND METHODS

6.1.1 PLANT MATERIAL AND TRANSFORMATIONS

Petunia plants were grown under standard greenhouse conditions. The pMADS1 and pMADS2 cDNA's were isolated from *Petunia hybrida* line W115. The fbpl gene was isolated from Petunia hybrida line R27 by Angenent et al., (Plant Cell 4:983–993 (1982)). The petunia 'green petal', gp, mutant line PLV was resulted from gamma-ray treatment and was kindly provided by Dr. E. Farch (INRA, Dyon, France). Other hybrid lines used were *Petunia hybrida* line V26 and V30. The presumed ancestor petunia lines used were; *Petunia axillaris* (S1 and S2, the different S numbers designate different origins), *Petunia inflata* (S6 and S14), *Petunia parviflora* (S4), *Petunia violacea* (S9 and S10), *Petunia integrifolia* (S12 and S13) and *Petunia parodii* (S8). These lines were kindly provided by Dr. R. Koes (Free University, Amsterdam, The Netherlands). Plant transformations were performed as described by Horsch et al., (Science 227:1229–1231 (1985)) using leaf discs from V26 (construct VIP162), a hybrid of V26 and PLV (construct J84) or PLV (construct VIP186).

6.1.2 DNA CLONING STRATEGIES

The pMADS1 and pMADS2 coding sequences were isolated from a petunia W115 cDNA library using a PCR fragment spanning the MADS-box region of the *Antirrhinum deficiens*-A gene. The overexpression construct J84 was made by cloning the pMADS1 cDNA fragment into a vector containing the CaMV 35S promoter and rbcS E9 3' termination and processing sequence (Halfter et al., 1993, J. Cell Biochem Suppl. Vol. 17, Part B, page 14). The pMADS1 pd-RNA construct VIP162 was made by cloning the cDNA as an XbaI-KpnI fragment downstream of a modified 35S (m35S) promoter in the vector pBSII (Stratagene) to generate clone VIP160. The modified 35S promoter contains the −90 to +8 fragment of the CaMV 35S promoter with 4 copies of the B3 domain (Benfey and Chua, 1990, Science 250:959–966) and 4 copies of an optimized AS-1 binding site (Katagiri et al., 1989, Nature 340:727–730) placed upstream. The m35S promoter has been shown to drive expression of a β-Glucuronidase reporter gene in all cell layers of the petunia petal. The m35S promoter plus pMADS1 coding sequence was isolated from VIP160 as a partial HindIII-KpnI fragment and cloned between the HindIII-KpnI site of the binary vector VIP26 (van der Krol and Chua, 1991, Plant Cell 3:667–675) to generate clone VIP162. The pMADS2 gene construct was made by inserting the EcoRI fragment of the pMADS2 cDNA into a binary vector which contains both the mCaMV-35S promoter and the rbcS E9 3' termination and processing sequence to form VIP186. The chimeric gene constructs that were introduced into the petunia genome are shown in FIG. 1.

6.1.3 SOUTHERN AND NORTHERN ANALYSIS

Genomic plant DNA, isolated from about 1 gram of leaf tissue, was digested with restriction endonucleases, size fractionated on agarose gels and blotted onto Genescreen-plus membrane (DuPont). The hybridization and washing conditions were similar as for the Northern blots (see below). Total RNA was isolated from plant tissue using the RNaid isolation procedure (BIO 101). Flower buds were dissected into first, second, third and forth whorl tissue. The young flower bud material examined measured, from base to the tip of the first whorl sepal, 5–15 mm for V26 and V30, 5–20 mm for W115 and 5–10 mm for PLV. In all lines, at this stage, the second whorl tissue is mainly light green in color and covers the third and fourth whorl organs and the third whorl stamen filaments have not elongated. The mature flower bud material consisted of closed flower buds 5–6 cm long for V26 and V30 (measured from the base to the tip of second whorl petal), closed flower buds 6–7 cm long for W115, and for PLV, open flowers with stamen filaments fully elongated, but before anthesis. For V30, V26, and W115, the mature floral bud stage coincides with the peak of CHS gene expression in the second whorl (Koes et al., 1989, Plant Mol. Biol., 12:213–225).

Equal amounts (7 μg) of total RNA were fractionated on 1.2% agarose gels containing 6% formaldehyde. Gels were blotted onto GeneScreen Plus (DuPont) according to the manufacturer's instructions and hybridized to random primed labeled DNA (Boehringer Mannheim) in 20% formamide, 5X SSC, 1% SDS, 5X Denhardts, 10 μg/ml salmon sperm DNA at 42° C. Blots were either washed under nonstringent conditions (0.5 hr., 2X SSC, 65° C.) or stringent conditions (0.5 hr., 0.2X SSC, 65° C.). Gene-specific probes (cDNA fragments without the MADS-box region) were used for each of the genes. The fbp1 probe, covering nucleotides 494–760 (Angenent et al., 1992, Plant Cell 4:983–993) was generated by polymerase chain reaction amplification using R27 genomic DNA as a template.

6.1.4 PHENOTYPIC ANALYSIS AND IMAGING

Flower and hand-made tissue sections were photographed under a NIKON SMA-U stereo microscope. Epidermal peels taken from sepal or petal tissue were vacuum infiltrated with water to remove air-pockets before photographing. The microscopic sections were made and stained as described by Natarella and Sink (Hort. J. Amer. Soc. Hort. Sci 96:600–602 (1971)) and photographed in bright field either under the NIKON SMZ-U stereo microscope or a NIKON optiphot microscope. All images were processed in Adobe Photoshop and assembled in Aldus Pagemaker. The Northern images were compressed vertically (20%).

6.2 RESULTS

6.2.1 THE WILD TYPE FLOWER

The flower development in petunia has been described in detail (Prior, 1957 Proceedings of the Iowa Academy of Science 64; Natarella and Sink, 1971, Hort. J. Amer. Soc. Hort. Sci. 96:00–602; Sink, 1984, Monographs on Theoretical and Applied Genetics 9; Turlier and Albovette, 1988, Can. J. Bot. 67,1985–1997). Because the transformations described here were done in the *Petunia hybrida* line V26, a short description will be given of the essential features of the V26 flower for the purpose of comparison with mutant or transgenic flowers. The mature flower of V26 (FIGS. 2 and FIG. 3, Panel A) has in the first whorl five sepals that are fused at the base to form a calyx tube (FIG. 3, Panel B). Regions in the calyx tube contain cells that make less chlorophyll as judged from the white color of the parenchyma cells. Growth of the corolla tube and of the filaments occurs in part under the zone of interpetalous initiation, resulting in congenital fusion of the filament to the corolla tube (FIGS. 2 and FIG. 3, Panel C). FIG. 3, Panel D, shows a stained cross section near the base of a 10-mm-long floral bud illustrating the fusion of the filament to the tube. From the point of separation the filaments become a smooth, round structure with flat, elongated epidermal cells that are lightly pigmented near the anther sacs (FIG. 3, Panel E).

The lower and upper epidermal cell layer of the sepal appear similar morphologically, consisting of jigsaw-shaped epidermal cells, stomata and trichomes (FIG. 3, Panel F). The inner and outer epidermal cell layer of the corolla tube are comprised of flat, elongated cells that may be pigmented (FIG. 3, Panel G) and trichomes are only present on the outside of the corolla tube (see FIG. 3, Panel C). On the limb, trichomes are only found on the lower epidermis and are mainly associated with the main vascular bundles. At the upper epidermal cell layer of the limb the cells are round, cone-shaped, and pigmented with anthocyanin (FIG. 3, Panel H). In contrast, the epidermal cells at the lower side of the limb vary from jigsaw-shaped to round (FIG. 3, Panels I and J) and may have the characteristic cone-shape of the upper epidermal cells. Near the main vein the lower epidermal cells are not always pigmented (FIG. 3, Panel J).

6.2.2 THE gp (PLV) FLOWER

The petunia gp mutant is characterized by a homeotic conversion of the second whorl petal into sepal. The gp phenotype was obtained in plants by a spontaneous mutation (line M64), by ethylmethane sulfonate (EMS) treatment (line R100) and by gamma radiation mutagenesis (line PLV). All these mutations are recessive. A description is given here of the flowers of the gp line PLV (de Vlaming et al, 1984, Plant Mol. Biol. Reporter, 2:21–42). Sections of young flower buds (up to 3 mm long, measured from the base to the tip of the first whorl sepals) of V26 and gp (PLV) are almost indistinguishable morphologically (FIG. 4 cf. Panel A with Panel B). In both V26 and gp (PLV) trichomes begin to develop on the abaxial face of the second whorl organs when the flower buds are about 2 mm long. When the gp (PLV) floral buds are about 4 mm long, the formation of trichomes can be detected at the adaxial face of the second whorl organs, whereas no trichomes are detected on the adaxial face of the V26 second whorl petal at this or at any later stage of flower development. FIG. 4, Panel C and Panel D, show a cross section through a 15-mm-long flower bud of V26 and of gp (PLV), respectively. The parenchyma cells of the second whorl organ in gp (PLV) are not as large as those of the first whorl sepal but smaller than those of the petal, and the cell wall staining is more like that of sepal than petal (FIG. 4, Panel E and Panel F).

FIG. 5, Panel A shows the mature flower of gp (PLV). The first whorl sepals are fused at their base, as in V26, and near the base, show only a very slight reduction in chlorophyll pigmentation as compared to the V26 sepals (compare FIG. 5, Panel B with FIG. 2, Panel B). The upper and lower epidermal cell layer of the gp (PLV) first whorl sepal are similar to those of the V26 sepal. The gp (PLV) second whorl sepals are slightly thinner than the first whorl sepal tissue and show no marked reduction of chlorophyll synthesis near their base (FIG. 5, Panel C). FIG. 5, Panel D and Panel E, show an epidermal peel from the abaxial and adaxial face of the second whorl sepal, respectively. The epidermal cells on both faces resemble those of the V26 sepal (jigsaw-shaped cells, stomata and trichomes). Thus, the second whorl organs of gp (PLV) are sepals by virtue of their green pigmentation, cell size and shape, and the presence of trichomes and stomata on both faces.

Although stamen development in the gp (PLV) mutant is similar to that in wild-type petunia and leads to the formation of anther sacs which produce viable pollen, some developmental differences are apparent. In contrast to V26, the stamen filaments of gp (PLV) are not fused to the second whorl (FIG. 5, Panel F, see also cross-section in FIG. 4, Panel D). Sepaloid structures however, often emerge from the third whorl stamen (FIG. 5, Panel G) or additional sepaloid third whorl organs are initiated between the stamen filaments (FIG. 5, Panels H and I). Upon maturation of the gp (PLV) flower (after anthesis has occurred) these green sepaloid structures develop regions with petaloid characteristics: cone-shaped cells with anthocyanin (FIG. 5, Panel H). Also, frequently petaloid epidermal cells and/or trichomes were detected on the stamen filaments (FIG. 5, Panel J) which clearly differ from the long, elongated epidermal cells found on wild-type stamen filaments (FIG. 3, Panel E). The occurrence of the extra sepaloid structures and sepal/petaloid stamen in the third whorl may vary throughout the plant life cycle and may be influenced by growth conditions.

6.2.3 MADS box gene expression

The expression patterns of the five petunia MADS box genes were analyzed. The pMADS1, pMADS2, and pMADS3 genes are expressed in flowers but not in vegetative organs, whereas the pMADS4 gene is expressed in leaves as well as in flowers. The expression pattern of fbpl in petunia has been reported previously by Angenent et al. (Plant Cell 4:983–993 (1992)). Initial experiments showed that the steady-state mRNA levels of the different floral organs vary throughout development. Therefore the expression levels at early and late stages of development were examined (for a description of stages, see Materials and Methods (Section 6.1)). These initial studies also showed that the steady-state mRNA levels of some pMADS box genes may vary at similar stages of floral development among different lines, presumably reflecting the different rates at which floral organs mature in different genetic backgrounds. Two processes that are specifically associated with petal development are suppression of chlorophyll synthesis and enhancement of anthocyanin pigmentation in the petals. To monitor these events, the expression of the chlorophyll a/b binding protein I CAB) gene and the chalcone synthase (CHS) gene were monitored. For easy comparison, the expression profile in V26 (FIG. 6, Panels A to G, top sections) and gp (PLV) (FIG. 5, Panels A to G, middle sections) floral tissue were grouped for each of the MADS box genes.

pMADS1 In V26 this gene is mainly expressed in the second and third whorls (FIG. 6, Panel A, top section). No expression could be detected in gp (PLV), either at an early or late stage of flower development (FIG. 6, Panel A, middle section).

pMADS2 FIG. 6, Panel B, (top section) shows that the expression of this gene in V26 is mainly in the second and third whorls. In the second whorl tissue of gp (PLV), this gene is expressed at a very low level and only at young stages of flower development (FIG. 6, Panel B, middle section), whereas its expression of the third whorl (stamens) is increased in both young and mature gp (PLV) floral buds compared with that in V26.

fbpl In V26 the fbpl gene, like pMADS2, is expressed in the second and third whorls (FIG. 6, Panel C). In gp (PLV), fbpl expression is only detected in the second whorl at a very low level in early stages of development, whereas no expression is detected at the late stage of second whorl development. However, in the third whorl of gp (PLV), fbpl expression is elevated both in young and mature flower buds compared with that in V26 (FIG. 6, Panel C, middle section).

pMADS3 FIG. 6, Panel D, shows that this gene is expressed in the third and fourth whorls of V26 (FIG. 6, Panel D, top section) as well as in gp (PLV) (FIG. 6, Panel D, middle section). In the fourth whorl of gp (PLV) the mRNA level is slightly higher than in the wild-type V26.

pMADS4 The expression of this gene is mainly detected in the first, second, and fourth whorls of V26 flowers (FIG. 6, Panel E, top section). Expression in the mature second whorl is lower and in the mature fourth whorl is higher in gp (PLV), compared with V26 (FIG. 6, Panel E, cf. top and middle sections).

CHS expression is detected in all four whorls of the V26 flower, but the expression is elevated in the mature petal tissue. In the mutant gp (PLV) the CHS gene is also expressed in all four whorls (FIG. 6, Panel F, middle section); however, its up-regulation in the mature second whorl is no longer detected. In contrast, in the third whorl of the gp (PLV) flowers, the CHS expression level is higher compared with that of mature stamens of V26.

CAB The CAB gene expression is high in the first two whorls of both V26 (FIG. 6, Panel G, top section) and gp (PLV) (FIG. 6, Panel G, middle section). In the mature wild-type flower the CAB gene expression level diminishes in petals and carpels and the mRNA is not detected in mature stamens.

6.2.4 gp (PLV) MUTANT CONTAINS A pMADS1 DELETION

The lack of any pMADS1 expression in gp (PLV) prompted an examination of its genomic DNA for the state of the pMADS1 gene. FIG. 7 shows the hybridization profile of a pMADS1 probe to genomic DNA of three wild-type hybrid lines (V26, V30, and W115) and a segregating population of gp mutant and wild-type plants (4 of 20 plants analyzed are shown). DNA isolated from gp plants did not hybridize to the pMADS1 probe, demonstrating that this gene is deleted from the genome. Therefore, gp (PLV) is a null mutant for pMADS1. This is not surprising because the mutation in gp (PLV) was induced by gamma radiation treatment, which is known to cause chromosomal deletions. Under low stringency hybridization conditions, the pMADS1 probe detected no additional bands that were present in the wild type and absent from the gp mutant, indicating that no other pMADS1-related gene is deleted from the gp genome. The other four petunia MADS box genes are present and intact in the mutant genome, as confirmed by Southern and Northern blot analyses (see above). The gp (PLV) phenotype is a phenotypic marker for chromosome IV of *P. hybrids*, thus placing the pMADS1, gene on chromosome IV (de Vlaming et al., 1948, Plant Mol. Biol. Reporter 2:21– 42). The 'green petal' phenotype has also been obtained by EMS treatment of petunia seeds (line R100). Southern analysis of this mutant did not reveal any difference between mutant and wild type pMADS1 restriction fragments.

6.2.5 pMADS1 RESTORES NORMAL FLOWER DEVELOPMENT

To prove that pMADS1 is an essential gene for petunia petal development it was necessary to show that the gp phenotype can be complemented by the pMADS1 gene function. Because of regeneration problems associated with gp (PLV), a cross between this mutant and V26 was made. A plant (GP/gp) from the progeny was used for leaf disc transformation to introduce a 35S-pMADS1 gene (J84; see Materials and Methods (Section 6.1)). One of the resulting transgenic plants, carrying three independent inserts of J84 and showing an over-expression phenotype (Halfter et al., 1993, J. Cell. Biochem. Suppl. Vol. 17, Part B, Page 14; FIG. 8, Panel A), was backcrossed to gp/gp (PLV) plants. The progeny plants were analyzed for the presence of the wild-type pMADS1 gene and the 35S-pMADS1 transgene by Southern blot hybridization and for their floral phenotype. Among the 33 progeny plants analyzed, three plants were identified that neither contained a wild-type pMADS1 gene nor a 35S-pMADS1 transgene in their genome, and these plants had a gp phenotype. Ten other plants did not contain any wild type pMADS1 gene but had one or more copies of the 35S-pMADS1 transgene. Four of these still exhibit the gp phenotype, suggesting a lack of complementation in one of these plants in (M1a). One plant showed small red sectors on a sepaloid second whorl (plant M1b, FIG. 8, Panel B), indicating a partial restoration by the 35S-pMADS1 transgene. At a later stage this same plant showed a very weak restoration.(FIG. 8, Panels C and D; before and after anthesis, respectively). FIG. 8, Panels G and H, shows that the late differentiation into petal tissue in the second whorl tissue of M1b resulted in the presence of trichomes on the upper epidermal layer of the petal limb. Three plants showed nearly complete (e.g., M1c FIG. 8, Panel E) and two showed complete (e.g., M1d FIG. 8, Panel F) petal development in the second whorl. In these plants the mutation rate of the petal was clearly slower compared to that of V26 (FIG. 8, Panels J and K). The late restoration resulted in trichomes being present on the adaxial face of the petal tube in plant M1c (cf. inner face of wild-type tube (FIG. 8, Panel L) with that of M1c tube (FIG. 8, Panel M)). FIG. 8, Panel I, shows that the cells constituting the second whorl sepal structure in the gp flowers can still be recognized in flowers of plants that showed partial complementation (M1c). In plants that showed no or weak restoration of the pMADS1 gene function in the second whorl, the ectopic expression of the 35S-pMADS1 gene in the third whorl did not suppress the development of extra organs. However, these extra organs in the third whorl and structures on the stamen, which in gp (PLV) only partially showed petal characteristics, then developed into full petaloid tissue (FIG. 8, Panel N). Unlike the filaments of the gp (PLV) flowers, the base of the filaments of the M1c and M1d flowers were fused to the second whorl tissue, as in V26.

FIG. 9, Panel A shows a Northern blot analysis of RNA isolated from mature flowers of M1a plants, the M1c plus M1d plants. In both sets of plants, the pMADS1 transgene shows high expression of the first two whorls and low expression in the inner two whorls. The expression of the transgene in M1a is very low (expression in the third and forth whorl is only visible after prolonged exposure), which correlates with the lack of restoration in petal development in these transgenic plants. In the M1c and M1d plants, the restoration of petal development correlated with a high expression level of the 35S-pMADS1 transgene, as well as an up-regulation of pMADS2 and fbp1 expression in the second whorl, indicating the expression of these genes in this whorl is controlled by PMADS1. Overexpression in petunia gp (PLV) of a similar pMADS2 gene construct (see Materials and Methods (Section 6.1)) did not result in any restoration of petal development nor did it affect expression of fbp1 (FIG. 9, Panel B).

6.2.6 "pMADS1" pd-RNA CONSTRUCT SUPPRESSES pMADS1 EXPRESSION

Supporting evidence for the function of the pMADS1 gene in flower development was obtained from V26 transgenic plants in which introduction of a m35S-pMADS1 pd-RNA construct resulted in a suppression of pMADS1 expression, in some cases leading to a complete phenocopy of gp. The suppression of pMADS1 was manifested in a gradation of phenotypes ranging from a decrease in petal pigmentation (5 out of 20 transgenic plants, SD15; see FIG. 10, Panel A), reduced petal growth (1 out of 20, SD6; see FIG. 10, Panel B), reduced growth and differentiation (1 of 20, SD12; see FIG. 10, Panel C) to a complete lack of petal differentiation, resulting in sepaloid structures in the second whorl (1 of 20, SD3; see FIG. 10, Panel D). A partial petal differentiation of the second floral whorl in SD3 plants could occur with the aging of the plant (mainly after anthesis), resulting in slightly pigmented sepaloid second whorl structures (SD3, FIG. 10, Panel E). In all of the transgenic plants mentioned above, the suppression resulted in the formation of third whorl stamen with filaments that were not fused to the second whorl (e.g., see SD12; FIG. 10, Panel F). Also, in the case of a strong suppression phenotype, the third whorl organ number was often altered by the appearance of small additional sepaloid structures between the stamen filaments (arrow, FIG. 10, Panel F). The partial petal differentiation in SD3, SD6, and SD12 in the second whorl differed by cell layer and could occur in sharply defined sectors (SD3; FIG. 10, Panel G). FIG. 10, Panels H, I, and J, show the different end stages of petal development that can be detected in these second whorl floral organs. In the epidermal peels the petaloid cells could be seen next to nonpigmented sepaloid cells, indicating that petal differentiation is cell autonomous (FIGS. 10, Panels I and J). On the plants with mild to strong suppression phenotype, the filaments of the stamen showed regions with petaloid cells, pigmented with anthocyanin, and occasionally a trichome (FIG. 10, Panel K).

The changed phenotype of the transgenic flowers is attributed to a suppression of the pMADS1 gene because the pMADS1 mRNA steady-state level was substantially reduced in these transgenic lines (see below). The suppression phenotype was stably inherited to the next generation for lines SD12 and SD3. The progeny from the selfed transgenic line SD15 showed a segregating population of plants among which petal development varied from wild-type (SD15a), medium petal development (SD15b) to sepaloid petals (SD15c). This was due to the segregation of three independent inserts of the m35s-pMADS1 transgene. Of 20 progeny plants, 3 showed a floral phenotype which was not consistent with a suppression of just the pMADS1 gene function. In these flowers the second whorl petals often did not develop or were fused to the third whorl stamen to form petaloid stamen (e.g., SD15d; see FIG. 10, Panels L and M).

6.2.7 RNA ANALYSIS OF PLANTS SUPPRESSED BY pMADS1 pd-RNA CONSTRUCTS

To demonstrate that the phenotype in the transgenic lines carrying the m35S-pMADS1 pd-RNA construct was due to a suppression of pMADS1 expression, the steady state levels of the different pMADS1 mRNAs were examined during floral development in SD15c, a transgenic line which showed a gp phenotype (FIG. 6, Panels A to G, bottom sections) and in SD15d, a transgenic line that showed a limited second whorl development and petaloid stamen (FIG. 6, Panel H). Because there was no clear separation between second and third whorl in SD15d, the tissues of these two whorls were combined for RNA analysis. In SD15c the pMADS1 mRNA steady state levels were much reduced both in the second as well as in the third whorl, indicating a suppression both of the pMADS1 transgene and the endogenous gene (FIG. 6, Panel A, cf. lanes 2 and 3 of top and bottom panels). The transgenic line SD15d had a much reduced pMADS1 mRNA steady state level in young floral buds, but the pMADS1 gene was not suppressed in later stages of floral development (FIG. 6, Panel G, top panel). The lack of a significant high steady-state level of pMADS1 mRNA in SD15c indicates that the change in flower phenotype in these plants was caused by a suppression of the pMADS1 trans- and endogenous genes.

To see whether the suppression effect was specific for the pMADS1 gene the expressions of pMADS2, pMADS3, pMADS4, and fbp1 were also analyzed. In young sepaloid tissue of the second whorl of SD15c, the pMADS2 and fbp1 steady-state mRNA levels were very low, but similar to those of V26. Upon maturation of this tissue, expression of both genes remained low, in sharp contrast with the increases in pMADS2 and fbp1 steady-state mRNA levels in mature petals of untransformed V26 flowers (FIG. 6, Panels B and C, cf. lane 2 of top and bottom panels). In line SD15d, pMADS2 and fbp1 expression in the second/third whorl increased upon maturation (FIG. 6, Panel H).

RNA analysis of V26 and gp (PLV) and the pMADS1 restoration plants indicated that both pMADS2 and fbp1 are regulated by pMADS1 (see above). Therefore, the lack of pMADS2 and fbp1 expression in the second whorl of SD15c is likely the result of the reduced pMADS1 gene expression in this whorl, rather than a nonspecific suppression effect of the 35S-pMADS1 pd-RNA construct. In the mature third floral whorl of gp (PLV) the expression of pMADS2 and fbp1 is elevated (FIG. 6, Panels B and C, middle sections). However, Northern analysis of SD15c showed that the pMADS2 gene expression is very low in the mature third whorl organs. This indicates that pMADS2 may also be a target for suppression by the pMADS1 pd-RNA construct. Also the phenotype of plant SD15d is stronger than that of gp (PLV), a pMADS1 null-mutant, suggesting that genes other than just pMADS1 are being suppressed at an early stage of flower development in SD15d. The suppression effect has little or no influence on pMADS3 and pMADS4 expression levels. (FIG. 6, Panels D and E, lower section; and FIG. 6, Panel H).

7. EXAMPLE: pd-RNA CONSTRUCT ENCODING A CHS cDNA SEQUENCE SUPPRESSES FLOWER PIGMENTATION IN PETUNIA

The suppression pattern conferred by a pd-RNA construct encoding sequences homologous to the chalcone synthase (CHS) gene was analyzed in petunia plants. CHS is a key enzyme in flavonoid biosynthesis. It catalyzes the formation of naringenin chalcone, an intermediate in the biosynthesis of flavonols, flavones, isoflavonoids and anthocyanins. In petunia, suppression of CHS expression alters flower pigmentation (Napoli et al., 1990, Plant Cell 2:279-289; van der Krol et al., 1990, Plant Cell 2:291-299). Transformation of wild-type petunia with a pd-RNA construct encoding a CaMV 35S promoter operably linked to a CHS cDNA segment without a functional 3' termination and processing sequence produces transgenotes with altered flower pigmentations indicative of CHS suppression. Analysis of the affected transgenotes show a reduction in the steady state level of the CHS mRNA.

7.1 MATERIALS AND METHODS

The chalcone synthase (CHS) cDNA fragment that was used in VIP189 and VIP190, was generated by PCR amplification using a full length CHS cDNA clone and the primers SK78 and SK79; SK78; 5'-AAAAAAGGATCCTAGA-TAGATAGCCATTGGAACAGCCACACCTAC-3' (SEQ ID NO:1) SK79; 5'-TTTTTTGAATTCAAAAGGAGGGA-CAGAAAGATAAGTCC-3' (SEQ ID NO:2) These primers amplify bases 115–1380 of the CHS sequence (Koes et al., 1986, Plant Mol. Biol. 12:213–225), including the AAUAAA polyadenylation signals in the 3' tail of the cDNA. The amplification deletes the first 50 bases of the open reading frame, including the initiation codon and introduces at this site stop-codons in all three reading frames (underlined in SK78). The PCR product was digested with XbaI and EcoRI and cloned into pBSII (Stratagene) to create VIP187 and into the XbaIEcoRI site of VIP40 (van der Krol and Chua, 1990, Plant Cell 3:667–675) to create VIP189. The CHS sequence was isolated from VIP187 as an XbaI-KpnI fragment and cloned into the XbaI-KpnI site of VIP40 to create VIP190.

7.2 RESULTS: "CHS" pd-RNA CONSTRUCT SUPPRESSES CHS EXPRESSION

To distinguish between the effect of the promoter and the 3' processing sequences on suppression, we first tested two CHS gene constructs that only differ in their 3' processing sequences (i.e., with and without rbcS E9 poly(A) addition signal). In the chimeric CHS gene constructs used, the initiation codon of the CHS coding sequence is mutated (see Section 7.1). Any mRNA from this transgene can not be translated into CHS enzyme. This mutation was made in order to obviate any confusions over the source of any CHS expressed in the transformants (i.e., any change in CHS activity or flower pigmentation must necessarily be due to changes in the expression of the endogenous CHS gene). Gene construct VIP189 (FIG. 11, Panel B) contains the CaMV 35S promoter, the mutated CHS coding sequence (i.e., absent the native initiation codon), and an rbcS E9 poly(A) addition signal. Based on prior studies, this construct is expected to suppress CHS gene activity in V26 flowers with a frequency of about 30% (see Napoli et al., 1990, Plant Cell 2:279–289). The other construct, VIP190 (FIG. 11, Panel C), consists of the CaMV 35S promoter, the same mutated CHS coding sequence, but no poly(A) addition signal. Constructs VIP189 and VIP190 were introduced into Agrobacterium tumefaciens, and Petunia were transformed using the leaf disc transformation method (Horsch et al., 1989, Science 227:1229–1231). Transgenic plants were selected on kanamycin and upon maturation transferred to the greenhouse.

Suppression of the endogenous CHS gene by the chimeric CHS transgene was scored by analyzing the petal pigmentation (purple; no suppression, white or partial purple; suppression). Southern analysis was used to verify the transformed state of the transgenic plants analyzed. This screening was particularly important in instances where a putative transformant showed no apparent change in phenotype. A total of ten independently transformed plants were identified for each gene construct.

Although the frequency of CHS suppression was relatively low for both CHS gene constructs, plants transformed with VIP190 showed a 70% higher incidence of suppression than plants transformed with VIP189. This result indicates that indeed a defective RNA processing signal is involved in increasing the suppression of homologous gene in transgenic plants. (See FIG. 11).

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosure of which are incorporated by reference in their entireties.

What is claimed is:

1. A method for producing a transformed petunia plant cell whose expression of a gene is suppressed, which method comprises:
   (a) transforming a petunia plant cell, that contains an expressible gene, with a recombinant DNA construct containing a DNA sequence encoding an RNA transcript in which 3' processing signal downstream of the polyadenylation addition site is omitted,
   wherein the transcription of said recombinant DNA construct results in a processing defective RNA transcript, and
   wherein the RNA transcript selectively hybridizes to said expressible gene; and
   (b) selecting a transformed petunia plant tell in which expression of the expressible gene is suppressed.

2. The method of claim 1 wherein said recombinant DNA construct further comprises a promoter operably linked to the DNA sequence encoding an RNA transcript.

3. The method of claim 1 wherein said suppressed expression results in altered pigmentation in petunia plants comprising said transformed petunia plant cells.

4. The method of claim 1 wherein said suppressed expression results in alteration of flower pigmentation in petunia plants comprising said transformed petunia plant cells.

5. The method of claim 1 wherein said suppressed expression results in inhibition of petal differentiation in petunia plants comprising said transformed petunia plant cells.

6. A plant regenerated from a transformed petunia plant cell produced in accordance with the method of claim 1.

7. A cell, tissue, organ, seed or progeny plant obtained from a plant produced in accordance with claim 6.

8. A method for producing a transformed petunia plant whose expression of a gene is suppressed, which method comprises:
   (a) transforming a petunia plant cell, that contains an expressible gene, with a recombinant DNA construct containing a DNA sequence that encodes an RNA transcript in which 3' processing signal downstream of the polyadenylation addition site is omitted,
   wherein the transcription of said recombinant DNA construct results in a processing defective RNA transcript, and
   wherein said RNA transcript selectively hybridizes to said gene;
   (b) selecting a transformed petunia plant cell;
   (c) regenerating a transformed petunia plant from said transformed petunia plant cell; and
   (d) selecting a transformed petunia plant in which expression of said gene is suppressed, wherein said suppressed expression results in inhibition of petal differentiation in petunia plants comprising said transformed petunia plant cells.

* * * * *